United States Patent
Milojevic et al.

(10) Patent No.: US 7,240,416 B2
(45) Date of Patent: Jul. 10, 2007

(54) PROCESS FOR MANUFACTURING ELECTRICALLY CONDUCTIVE COMPONENTS

(75) Inventors: Dusan Milojevic, Westleigh (AU); John Parker, Roseville (AU)

(73) Assignee: Cochlear Limited, Lane Cove, New South Wales (AU)

( * ) Notice: Subject to any disclaimer, the term of this patent is extended or adjusted under 35 U.S.C. 154(b) by 270 days.

(21) Appl. No.: 10/477,434

(22) PCT Filed: May 7, 2002

(86) PCT No.: PCT/AU02/00575

§ 371 (c)(1), (2), (4) Date: Nov. 7, 2003

(87) PCT Pub. No.: WO02/089907

PCT Pub. Date: Nov. 14, 2002

(65) Prior Publication Data

US 2004/0147825 A1  Jul. 29, 2004

(30) Foreign Application Priority Data

May 7, 2001 (AU) .................................. PR4818
Apr. 23, 2002 (AU) .................................. PS1924

(51) Int. Cl.
*H01S 4/00* (2006.01)

(52) U.S. Cl. ............... 29/592.1; 29/831; 29/844; 29/846; 29/858; 29/893.35; 29/894.353; 174/250; 174/254; 381/23.1; 451/11; 451/36; 451/41; 600/25; 600/372

(58) Field of Classification Search ............... 29/592.1, 29/831, 844, 846, 858, 893.34, 894.353; 381/23.1; 174/250, 254; 600/25, 372; 451/11, 451/36, 41

See application file for complete search history.

(56) References Cited

U.S. PATENT DOCUMENTS 3,792,523 A * 2/1974 Grunberger .................. 29/557

(Continued)

FOREIGN PATENT DOCUMENTS

DE  27 18 267  11/1978

(Continued)

OTHER PUBLICATIONS

"Development of silicon microelectrodes for cochlear implant technology"; Parker, J.R.; Harrison, H.P.; Clark, G.M.; Patrick, J.; Reinhold, O.; Optoelectronic and Microelectronic Materials And Devices Proceedings, 1996 Conference on Dec. 8-11, 1996; pp. 12-15.*

(Continued)

*Primary Examiner*—Paul Kim
(74) *Attorney, Agent, or Firm*—Christie, Parker & Hale, LLP

(57) ABSTRACT

A method of forming a device, such as an electrode array for a cochlear implant. The method comprises a step of forming a predetermined pattern of relatively electrically conductive regions and relatively electrically resistive regions in a sheet of biocompatible electrically conductive material, such as platinum foil. The method can comprise a step of working on the sheet to remove predetermined portions therefrom to form the one or more discrete relatively conducting regions. The step of working on the sheet can comprise embossing the sheet, cutting or slicing the sheet, or using electrical discharge machining (EDM) to remove unwanted portions of the sheet, the EDM equipment having a cutting tool comprising an electrode.

43 Claims, 19 Drawing Sheets

U.S. PATENT DOCUMENTS

| | | | |
|---|---|---|---|
| 4,532,930 A | | 8/1985 | Crosby et al. |
| 4,734,963 A | | 4/1988 | Ishiyama |
| 4,908,921 A | | 3/1990 | Chen et al. |
| 5,046,242 A | | 9/1991 | Kuzma |
| 5,343,616 A | * | 9/1994 | Roberts ........................ 29/846 |
| 5,575,885 A | * | 11/1996 | Hirabayashi et al. ......... 438/14 |
| 6,451,694 B1 | * | 9/2002 | Lim et al. ................... 438/683 |

FOREIGN PATENT DOCUMENTS

| | | |
|---|---|---|
| EP | 0 893 812 A2 | 1/1999 |
| EP | 1 050 269 A1 | 11/2000 |
| JP | 10-69905 | 3/1998 |
| JP | 2000-124383 | 4/2000 |

OTHER PUBLICATIONS

International Search Report of PCT/AU02/00575, dated Jul. 10, 2002.
Corresponding Australian application No. PR 4818 Search Report, dated Jul. 3, 2001.
International Preliminary Examination Report of PCT/AU02/00575, dated Aug. 12, 2003.
DT 2718-267 Derwent Publications Ltd., dated Feb. 11, 1978.

* cited by examiner

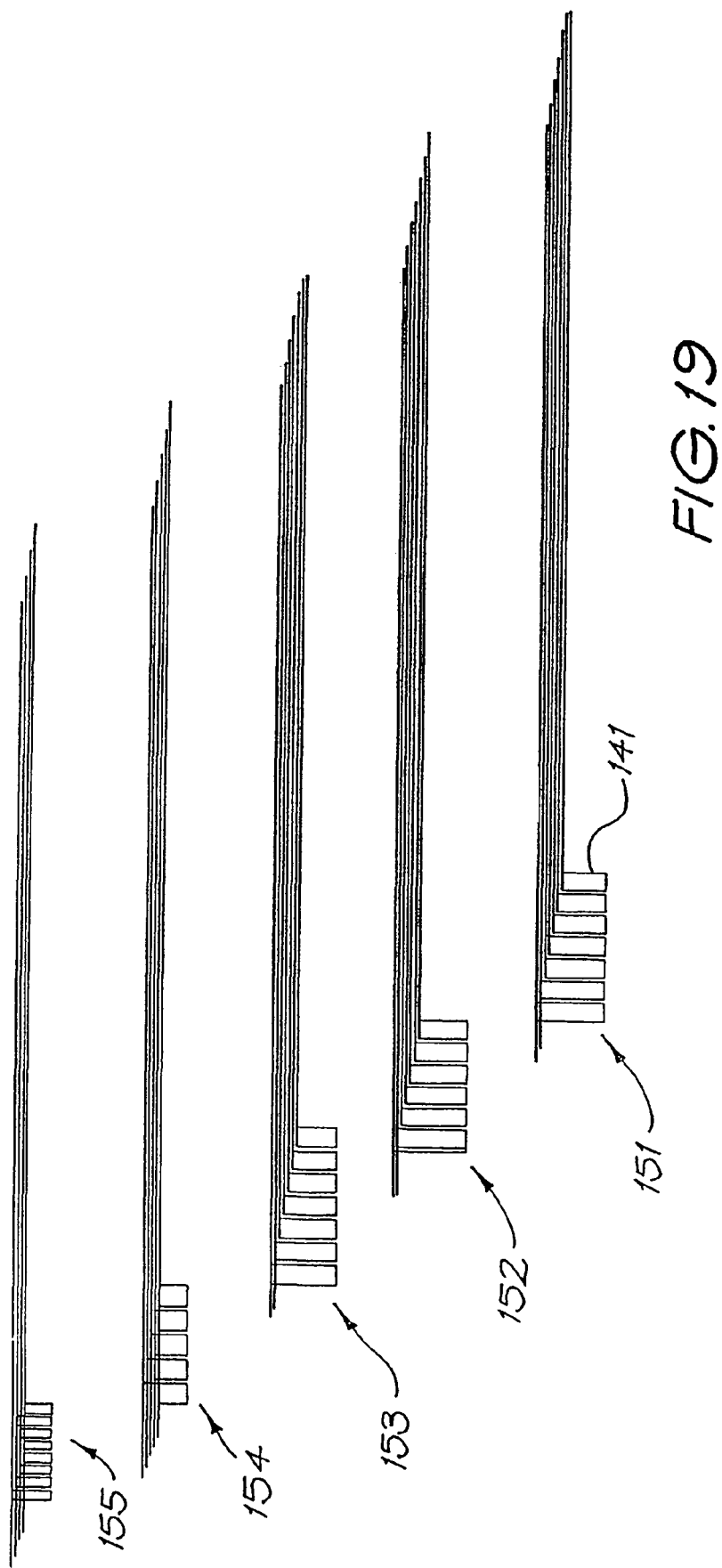

PROCESS FOR MANUFACTURING ELECTRICALLY CONDUCTIVE COMPONENTS

CROSS-REFERENCE TO RELATED APPLICATION

This application is a National Phase Patent Application of International Application Number PCT/AU02/00575, filed on May 7, 2002, which claims priority of Australian Patent Application Number PR 4818, filed on May 7, 2001, and Australian Patent Application Number PS 1924, filed on Apr. 23, 2002.

FIELD OF THE INVENTION

The present invention relates to a method of forming miniature wiring and connector systems for electrical products. More specifically the present invention relates to a method of forming electrode arrays, such as arrays for sensors, including biosensors, and implantable devices, such as an implantable recording or stimulating electrode or pad for use in the body. An electrode array formed using the method is also described.

BACKGROUND OF THE INVENTION

In many electrical devices, particularly those that are manufactured on a very small scale, the manufacture of the wiring and connector components is often a labour intensive and specialised craft. Ensuring that the wiring and connection of the various components of the systems occurs correctly is often the most expensive and labour intensive aspect of the manufacturing process, resulting in large costs associated with the time taken to manufacture the device which is often passed on to the ultimate consumer. This is also the case when such devices need to be specifically hand made to a specification as often the availability of the device is dependent upon the time taken to manufacture the device, with the time taken being difficult or impossible to expedite.

This is particularly the case in the field of medical implants and electrical devices that are implanted in the body to perform a specific task. Such devices may include: stimulating devices such as pacemakers, cochlear implants, FES stimulators; recording devices such as neural activity sensors and the like; implantable cables which may be used to connect implantable devices to other implantable devices or stimulating/sensing devices; diagnostic devices capable of carrying out in-vivo analysis of body parameters; and other types of implantable devices not yet contemplated. In such devices, the size needs to be minimised to ensure that they are minimally invasive upon implantation. As a result, in such instances, the electronic wiring and connections need also to be relatively very small. As such, manufacturing such devices to ensure that they are reliable and sturdy is a specialised art, and requires much time and expense.

As a result of the need to increase the miniaturisation of such devices, a wide range of techniques have been developed to create patterned components which would be too difficult or impossible to create by hand design and satisfy the high volume supply required. Techniques such as electroforming, vacuum deposition (sputtering, evaporation), and chemical vapour deposition, to name a few, are some of the known ways to produce patterned electrically conductive features on insulating surfaces on a micron scale. The problem with such methods however, has been that the metallic films produced by these techniques have been shown to feature properties that are different from the corresponding properties of the bulk materials used. This results in the desired materials functioning differently from their intended purpose, and in the particular case of platinum, the thin films have tended to crack and exhibit large impedance as well as a high degree of delamination.

In the manufacture of such devices, the bulk material is chosen based on the properties it exhibits. In the case of implantable electrical components, platinum has been found to exhibit particularly useful properties for such an application, namely good conductivity and inertness. With this being understood, it is beneficial in the manufacture of such devices for the bulk material to exhibit the same properties, especially physical properties, after manufacture as it did prior to manufacture, as discussed above. Variations in these properties can have a bearing on the functionality of the device, which, particularly in medical implanted devices, is highly undesirable. As mentioned, platinum films tend to crack and delaminate, hence delivering high impedance which impairs the functionality of the device. The use of thin film technology has been shown to work for a number of materials such as copper, gold and nickel, however none of these materials are suitable for active implantable devices.

Other more conventional methods of manufacturing such devices would be to directly stamp the desired components out of a conductive sheet using a fine blanking or stamping method. This is possible for applications whereby single components having large dimensions are stamped and the components do not need to be thin and flexible. However, simple stamping techniques are not suitable for multiple components having very small dimensions made out of thin conductive sheets, such as those proposed to be covered by the present invention. In such applications, the line width dimensions of the components and between the components are too small for stamping machines and the sheet material is too thin to provide the precision required for such components.

Because of these problems, medical implants, such as cochlear implants, are still manufactured using labour intensive manual procedures.

Hearing loss, which may be due to many different causes, is generally of two types, conductive and sensorineural. In some cases, a person may have hearing loss of both types. Of these types, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells.

In many people who are profoundly deaf, however, the reason for their deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No.

4,532,930, the contents of which are incorporated herein by reference, provides a description of one type of traditional cochlear implant system.

Typically, cochlear implant systems have consisted of essentially two components, an external component commonly referred to as a processor unit and an internal implanted component commonly referred to as a receiver/stimulator unit. Traditionally, both of these components have cooperated together to provide the sound sensation to a user.

The external component has traditionally consisted of a microphone for detecting sounds, such as speech and environmental sounds, a speech processor that converts speech into a coded signal, a power source such as a battery, and an external transmitter coil.

The coded signal output by the sound processor is transmitted transcutaneously to the implanted receiver/stimulator unit situated within a recess of the temporal bone of the user. This transcutaneous transmission occurs via the external transmitter coil that is positioned to communicate with an implanted receiver coil provided with the receiver/stimulator unit. This communication serves two essential purposes, firstly to transcutaneously transmit the coded sound signal and secondly to provide power to the implanted receiver/stimulator unit. Conventionally, this link has been in the form of a radio frequency (RF) link, but other such links have been proposed and implemented with varying degrees of success.

The implanted receiver/stimulator unit traditionally includes a receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes or stimulating pads, each electrode or pad being arranged and constructed to deliver a stimulating signal within a preselected frequency range to the appropriate cochlea region. The electrical currents and electric fields from each electrode or pad stimulate the nerves disposed on the modiolus of the cochlea. As the size of the cochlea is very small and the electrode assembly needs to be flexible enough to be inserted into the cochlea, the dimensions of the electrode assembly are such that do not allow for traditional manufacturing techniques.

For this reason, the intracochlear electrode array has generally been formed in a manual process by positioning a plurality (eg. 22) of electrically conductive platinum rings in a linear array and then welding electrical conductive wires to each of the electrodes or pads. This process can lead to small variations in the locations of the electrodes or pads and wiring from one manufactured array to the next with consequent small variations in the overall mechanical properties of the array once a resiliently flexible carrier member is moulded about the array. Each of the wires require connection to the receiver/stimulator unit and in order to ensure system integrity, each of the wires have been insulated from the others so that unwanted interaction between different electrical components is eliminated.

While the above method has proven very successful, it is labour intensive and hence a relatively expensive process. With implanted devices and miniaturisation becoming more common, there is an increasing need to provide electronic wiring and electronic connections in such systems that are both simple and reliable. The present invention is directed to a new method of forming such wiring and connections that addresses at least some of the problems with prior art processes.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention enables the manufacture of a multiplicity of components, where position of the individual components with respect to each other is predetermined and kept constant throughout the process, including the assembled final product. This is achieved without the use of traditional methods such as fine blanking and thin film technology/photolithography. The present invention relates to a method of manufacture of patterned features in the domain of microtechnology, wherein the properties of the chosen bulk metal are maintained throughout the manufacture of the device. The present invention also resides in a multilayered assembly and the method of assembly of the multilayered assembly.

The present application is directed to a method of forming electrical components for an electrical device. The method provides an advantage over the prior art in that it enables multiple electrical components to be formed in a simple and efficient manner, using materials and dimensions not possible with traditional mass production forming methods. The invention uses a sheet of material whose properties do not allow stamping out line widths as narrow as are required in the final assembly and allows multiple miniature components to be formed in very close proximity of dimensions not achievable through traditional stamping processes.

In a preferred embodiment, the present application is directed to a method of forming an electrode array for an electrode assembly. The method has potential advantages in providing a more efficient and inexpensive process of electrode assembly manufacture, particularly assembly of intracochlea electrode assemblies. The present invention further provides a method of forming an electrode array for an electrode assembly that preferably allows the manufacturing process to become automated or semi-automated so providing a desirable alternative to current manufacturing processes which require extensive labour input and increased manufacturing throughput.

In a first aspect, the present invention is a method of forming a device comprised of a predetermined pattern of relatively electrically conductive regions and relatively electrically resistive regions, the method comprising a step of:

(a) working a sheet of electrically conductive material to remove predetermined portions therefrom to form said one or more discrete relatively conducting regions, wherein said sheet of electrically conductive material has a thickness no greater than about 100 microns.

In this aspect, the step of working the sheet can include a step of pressing a sheet of electrically conductive material to form a predetermined raised pattern therein. One or more of the raised portions of the sheet can then, preferably, be removed to leave a remaining portion having a predetermined pattern. In another embodiment, those portions of the sheet not raised during the pressing step can be removed to leave a remaining portion having a predetermined pattern. In a still further embodiment, at least some of the raised pattern and at least some of the unraised portion can be removed to leave a remaining portion having a predetermined pattern.

Still further, the step of working the sheet can include a step of punching portions out of the sheet of electrically conductive material. In this embodiment, portions of the sheet are removed and separated from the sheet.

Yet further, the step of working the sheet can include a step of slicing or cutting the sheet of electrically conductive material.

In one embodiment, the remaining portion formed by the method can be used as an electrode array or a portion thereof. For example, the method can be used to form a layered component of an electrode array. The electrode array can comprise a plurality of stimulating pads or electrodes.

In yet another embodiment, the method can comprise an additional step of placing said remaining portion on a flexible carrier. Still further, the method can comprise the step of placing a plurality of said remaining portions on a flexible carrier to form an electrode array. In this embodiment, the plurality of remaining portions can be adapted to be formed into a layered configuration to form one or more electrode arrays.

In a preferred embodiment, the electrode array is for use as an implantable tissue-stimulating device. More preferably, the tissue-stimulating device is a cochlear electrode assembly, more preferably an intracochlear electrode assembly. In another embodiment, the electrode array could be used in a biosensor not necessarily related to an implanted device.

In one embodiment, the sheet of electrically conductive material is a biocompatible material. In a preferred embodiment, the sheet is a metallic material. Still further, the metallic material is a sheet of platinum. In a further embodiment, the sheet can be annealed. In a further embodiment, the electrode array is formed from a single sheet of electrically conductive material, such as platinum. In a further embodiment, more than one array can be formed from a single sheet of platinum. In yet a further embodiment the sheet could be a laminate of two or more layers (eg Pt & Ir), or could be an alloy.

The sheet preferably has a thickness between about 1 and 100 microns, more preferably between about 10 and 50 microns. The method preferably uses a sheet of platinum having a thickness no greater than 50 microns, more preferably no greater than 20 microns. Other suitable thicknesses can be envisaged. Each sheet can have dimensions of about 50 mm×250 mm. The size of the sheet will though depend on the requirements of the tooling used to work the sheet. As such, sheets of different dimensions can be envisaged. Generally it has been found that traditional stamping techniques have proven difficult to perform with the required accuracy upon sheets of material less than 50 microns, where the presence of a shear lip is a problem.

Still further, a plurality of electrically conducting connecting means can extend away from the stimulating pads of the electrode array. Each stimulating pad of the electrode array preferably has at least one connecting means extending away therefrom. More than one connecting means can extend from some or all of the stimulating pads in the electrode array.

The connecting means are preferably linearly aligned for a majority of their length extending away from the electrode array. In one embodiment, the connecting means can be disposed for at least a portion of their lengths in a parallel arrangement. Where the electrode array is formed from a single sheet, the plurality of connecting means are also preferably formed from that sheet and are integrally connected to respective electrodes in the array.

The sheet of conductive material can before the working step be a planar sheet. Sheets that already have folds or embossments formed therein prior to the working step of the present invention can, however, also be envisaged.

In producing an electrode array, it is firstly desirable to determine the configuration of the stimulating pads desired for the electrode array. Once the configuration is determined, the step of working the sheet can comprise using an embossing tool that is fabricated for use in the method so as to produce the desired electrode array configuration. Details of one possible type of embossing tool will be provided in more detail below.

In a preferred process, a planar sheet is placed relative to an embossing tool in a pressing means. The pressing means can be programmable to press a predetermined pattern in the sheet. Where the embossing tool is horizontally or substantially horizontally aligned, the planar sheet can be placed relatively above the embossing tool or relatively below the embossing tool. Where the embossing tool is vertically or substantially vertically aligned, the planar sheet can also be disposed in a vertical or substantially vertical alignment beside the embossing tool.

In one embodiment, the planar sheet can be moved relative to the embossing means and the pressing means and so be brought into position within the pressing means. In another embodiment, the embossing means and/or the pressing means can be moved relative to the planar sheet to relatively bring the planar sheet within the pressing means. In one embodiment, the process can be a continuous process, wherein a continuous sheet is fed through the pressing means.

The pressing means can include any medium having suitable properties to press the sheet of material and form the raised pattern therein. In one embodiment, the pressing means can be formed of a material with relatively low compressibility, such as a liquid, or gel having a relatively high content of liquid whilst retaining sufficient fluidity to occupy the available space. In another embodiment, compressed gas can be used to press the planar sheet against the embossing tool.

In one embodiment, the raised pattern is formed by a single pressing of the sheet. In another embodiment, the raised pattern can be formed by two or more pressings of the sheet. Where the raised pattern is formed by two or more pressings, the second or greater pressing of the sheet can be performed by the same embossing tool or a different embossing tool to that used for the first pressing. Where there are two or more pressings, the sheet may remain stationary between pressings or be relatively moved to a new press for each pressing of the sheet.

In a preferred embodiment, the pressing means used in the method has at least one relatively movable platen. The relatively movable platen preferably moves relative to a stationary platen. The embossing tool is preferably mounted to the stationary platen of the press.

Where the platens are horizontally disposed, the lower platen is preferably stationary and the upper platen preferably moves downwardly and upwardly relative to this stationary platen. In this embodiment, the embossing tool is preferably placed on the lower platen.

In one embodiment of the method, the sheet is placed above and on the embossing tool. A layer of backing material is then placed on top of the sheet before operation of the press. The layer of backing material can comprise a layer of a resiliently flexible polymeric or elastomeric material. The backing material can comprise a sheet of silicone or rubber and in another embodiment the backing material can be used as an integral part of the device. In a situation where the backing material is used as an integral part of the electrode array, the backing material must be suitable for implantation purposes, eg silicone.

In another embodiment, a lubricant can be used to improve the quality of embossed pattern. The lubricant is preferably suitable for an implant to avoid the cleaning step. Ethanol could be a suitable lubricant since it evaporates quickly and is in fact used as a washing agent in the assembly of implantable devices. A thin layer of the lubricant can be present between the embossing tool and the foil, and between the foil and the backing, or preferably both.

The pressing means can preferably apply differing levels of pressure to the sheet of the electrically conducting material placed on the embossing tool. For example, the pressing means can apply an initial pressure for a first predetermined period of time and then apply a second different pressure for a further predetermined period of time. The second pressure can be greater or lower than the initial pressure. The further predetermined period of time can also be less than, greater than or the same as the first predetermined period of time. In another embodiment, the pressure applied by the pressing means can continue to gradually increase throughout the embossing step.

In the method, the embossing tool with the embossed sheet and protective layer positioned thereon, can be relatively removed from within the pressing means. Following pressing of the sheet of electrically conducting material, the layer of protective material can be removed from the embossed sheet. The layer of protective material is preferably removed from the embossed sheet before the sheet is removed from the embossing tool. In another embodiment, the protective layer is retained on the sheet through later processing steps.

As described, once the sheet has been pressed to form a raised pattern therein, unwanted portions of the sheet can be removed. The unwanted portions can be removed by any number of ways, such as by cutting or by an abrading means.

It is envisaged that the cutting step can be performed at the same time as the pressing of the sheet of the conductive material. In this case the pressure applied to the sheet can be adjusted so as to be sufficient to cause the cutting of the sheet over the sharp edges of the embossing tool. In such an embodiment, the embossing tool is design to feature sharp edges that favour cutting the sheet. The cutting step is preferably performed relatively quickly. In a further embodiment, the sheet is preferably cooled prior to cutting. In one embodiment, the sheet can be cooled by liquid nitrogen prior to cutting.

In a still further embodiment, the sheet can be clamped to the embossing tool at the location of the protrusions of the tool.

The abrading means can preferably abrade or grind the unwanted portions from the sheet. It will be appreciated that the step of abrading the unwanted portions of the sheet may comprise more than one step. For example, a relatively coarse first abrading step may be firstly performed to move relatively large pieces of the unwanted portion of the sheet. Once this first step is complete, removal of finer pieces can be made by one or more additional abrading or polishing steps. In one embodiment, each additional abrading step removes finer pieces of the sheet than the preceding step. These additional steps ensure that the dimensions and shape of the remaining portions of the sheet match the originally desired configuration.

To prepare the embossed sheet for removal of the unwanted portion, the embossed sheet can be adhered by a layer of an adhesive to a support base. The adhesive is preferably a material that can be used to reversibly anchor the embossed sheet to the base. In one embodiment a PVA (polyvinyl alcohol) based adhesive is used that can hold the embossed sheet in place and, after the removal of the unwanted material, can be dissolved in water, freeing the said structure. In another embodiment, the preferred adhesive is an electrodisbonding adhesive. In this case, the support base must be electrically conducting. The support base can be formed from a group consisting of high-alloy steel, carbon steel, stainless steel, aluminium, aluminium alloys, copper, and titanium.

In one embodiment, the electrodisbonding adhesive is an epoxy resin formulation capable of forming relatively high strength adhesive bonds with conductive substrates but which can be relatively rapidly released through the application of a low voltage current. Disbonding preferably occurs via electrochemical reactions induced at the interface between the cured adhesive and the bonded substrate.

To adhere the embossed sheet to the support base, a quantity of adhesive is preferably firstly placed on a surface of the support base. Support spacers for a top plate are preferably positioned on the base plate around the border of the adhesive. The spacers can be relatively short. For example, the spacers can have a height of between about 1 and 1000 microns, more preferably about 150 microns.

Once the adhesive and spacers are in place, the embossed sheet is preferably placed on the adhesive. In one embodiment, the embossed sheet is placed on the adhesive such that the raised pattern extends outwardly away from the adhesive. In an alternative embodiment, the embossed sheet is placed on the adhesive such that the raised pattern extends inwardly into the adhesive.

Once the embossed sheet is in position, a top plate is then preferably placed on top of the embossed sheet and pressed downwardly until it rests on the spacers. The top plate is preferably formed from the same material as the base plate. A different material for the top plate could, however, be utilised. The top and bottom plate should be substantially parallel with respect to each other.

Once the adhesive is cured, the top plate and spacers can be removed. The support base, with the embossed sheet adhered thereto, is then ready to undergo further processing as defined above.

Where the raised pattern extends outwardly away from the support base, the abrading means will preferably remove a portion of the raised pattern formed in the sheet. Where the raised pattern extends inwardly into the adhesive, the non-raised portion of the sheet, or at least a portion thereof, will preferably be removed by the abrading means.

The remaining portion of the sheet left after the abrading step preferably comprises a plurality of electrically independent portions that preferably serve as stimulating pads of the electrode array. Where desired, the remaining portion also serves to provide the electrical connection means to the formed stimulating pads.

As previously defined, the step of working the sheet can include a step of punching portions out of the sheet of electrically conductive material. In one embodiment, the sheet of electrically conductive material, such as the platinum sheet defined herein, can be coated on a layer of resiliently flexible material, preferably a biocompatible resiliently flexible material like a silicone. A punch means fabricated so as to punch out a desired portion of the sheet is preferably brought into engagement with the sheet and punches out a desired portion. In a preferred embodiment, the stroke of the punch is such that the punch pushes the desired portion into the silicone layer where it can remain embedded.

In one embodiment, the step of punching out portions can comprise one use of a punch. In another embodiment, multiple uses of a punch may be necessary to form a predetermined pattern in a sheet. In another embodiment, the punch can be adapted to punch different portions of the sheet to different levels within the resiliently flexible layer.

This embodiment has the advantage of potentially forming two or more conductive layers from a single sheet of electrically conductive material.

As also previously defined, the step of working the sheet can include a step of slicing or cutting the sheet of electrically conductive material. In this embodiment, a cutting or slicing tool can be fabricated to form appropriate cuts in the sheet of electrically conductive material so resulting in the formation of a predetermined pattern of electrically conductive regions. In using such a tool, he sheet of electrically conductive material, such as the platinum sheet defined herein, can be coated on a layer of resiliently flexible material, preferably a biocompatible resiliently flexible material like a silicone. The cutting tool can be constructed so as to be relatively driven into contact with the surface of the platinum sheet. The tool can further be fabricated so as to drive at least a portion of the sheet into the resiliently flexible material.

In one embodiment, the method can further include the step of encapsulating at least one surface of the embossed sheet. In a preferred embodiment, the abraded surface of the sheet can be encapsulated in an electrically insulating material. This material is further also preferably bicompatible and resiliently flexible. One example of a possible encapsulating material is silicone.

Once the silicone is cured, the subassembly is removed from the "reversible" adhesive. In the case of the PVA adhesive, this can be removed by applying a certain quantity of water to dissolve away the PVA-based adhesive.

Once disbanded, the result is a plurality of separate electrically independent conductive portions having a layer of silicone encapsulated on one side thereof. If desired, the formed electrode array can undergo further processing, including washing and drying, to render it suitable for implantation as an intracochlea electrode assembly.

In another embodiment, the embossing tool can be retained in contact with the sheet of electrically conductive material. With the embossing tool in place against one face of the embossed sheet, the other face of the sheet can be encapsulated with at least a first layer of resiliently flexible material. This layer of material can comprise a layer of a polymeric or elastomeric material, such as a silicone or rubber. In a further embodiment, more than one layer of encapsulating material can be coated on the other face of the embossed sheet. The selected encapsulating material is preferably adapted to adhere strongly to the other face of the sheet. If necessary, a suitable silicone/metal adhesive can be used to ensure the encapsulating silicone layer remains in contact with the other face on subsequent removal of the embossing tool from said one face of the sheet.

With the embossing tool removed, the one face can then be subject to the abrading step of the process with at least a portion of the sheet not comprising part of the raised pattern therein being abraded from the sheet. If necessary, the encapsulation on the other face of the sheet can be rapidly cooled, such as by immersion in liquid nitrogen, to stiffen and harden the encapsulation prior to and/or while the abrading step is being performed.

In another embodiment, the removal of the embossing tool is not required. The embossed sheet in this embodiment is kept in close proximity of the embossing tool after the embossing process. In this embodiment the embossing tool is a disposable item and it is preferably fabricated using a low cost process to minimise the cost thereof.

As a result of the abrading step, a plurality of electrically separated stimulating pads and appropriate conducting means for each pad are formed. A layer of silicone or other suitable resiliently flexible and preferably biocompatible material is then used to form an encapsulation of the abraded side of the sheet. While this layer of encapsulation should encapsulate the electrical conduction means, it is preferred that the formed stimulating pads are not encapsulated. Accordingly, the mould used in the moulding of this encapsulation can incorporate upstanding insets that extend outwardly from the mould and which are aligned with the positions of the formed stimulating pads. These insets preferably abut the pads and so prevent the encapsulation covering the pads during the encapsulating process.

In one embodiment, two or more arrays formed using the method can be laminated together to form a single tissue stimulating electrode assembly. In one embodiment, the assembly can be formed from a first lamination having 7 electrodes, a second lamination having 8 electrodes and a third lamination having 8 electrodes, to form an electrode assembly having 23 electrodes. In the case of a cochlear electrode array, the formed array will preferably have 22 intracochlea electrodes and one extracochlea electrode. Such a lamination process preferably results in a linear array of the 22 electrodes.

In a further aspect, the present invention is a tool for use in the method as defined herein. In one embodiment, the tool can be an embossing tool.

In a preferred embodiment of this aspect, the tool is formed from a material that will emboss the electrically conducting sheet used in the method. Where the sheet is thin platinum sheet, the embossing tool can be formed from a metal material, such as a copper, or another material such as silicon wafer, or suitable plastics such as polycarbonate or polyimide.

The embossing tool will have a plurality of protrusions formed therein. The shape, dimension and position of the protrusions represent the raised pattern to be formed in the sheet of electrically conducting material. In the case of the silicon wafer, the protrusions can be etched in the wafer. In the case of a metallic embossing tool, the protrusions can be fabricated through use of laser micromachining. The plurality of protrusions can be adapted to form embossings in the sheet that are later removed from the sheet. In another embodiment, the protrusions can be adapted to form embossments that are not later removed from the sheet.

As an example only, to form a plurality of parallel linearly disposed electrical conduction means, the embossing tool preferably has a series of protrusions extending for a length in side-by-side relationship. The protrusions can narrow in thickness from their base to their top. In one embodiment, each protrusion at its base can have a thickness of between about 48 and 54 microns. At the top, each protrusion can have narrowed in thickness to between about 28 and 30 microns. The distance between adjacent protrusions at the base can be between about 65 and 67 microns, while the distance between the protrusions at the top is between about 86 and 87 microns. Each protrusion can have a height of about 30 microns.

Each ridge preferably ends in a pad protrusion adapted to emboss the electrically conductive sheet in a manner suitable to form a stimulating pad. The protrusion is preferably substantially rectangular in shape. To allow the formation of a longitudinal electrode array, each ridge preferably turns just prior to its join with its respective electrode protrusion. The turn in the ridge can be smoothly curved.

In a further embodiment, the plurality of aligned protrusions for the electrical conduction means extend linearly away from the pad protrusions for a length. The protrusions then further preferably spiral inwardly in ever decreasing circles. At an end distal the pad protrusion, each protrusion preferably terminates in a feedthrough electrode protrusion. The distal protrusion preferably forms an electrode for connection to the feedthrough of a receiver/stimulator means that will preferably be electrically connected to the electrode assembly formed using the tool.

In one embodiment, each embossing tool can have two sets of protrusions formed therein to allow creation of two electrode arrays from a single sheet of electrically conducting material, such as platinum.

According to a still further aspect, the present invention is directed to another invention comprising a method of forming a device comprised of a predetermined pattern of relatively electrically conductive regions and relatively resistive regions, the method comprising the steps of:

(i) coating at least a first surface of a sheet of electrically conductive material with at least a first layer of another electrically conductive material;

(ii) forming a predetermined pattern in the sheet of electrically conductive material by removing portions of the sheet therefrom such that at least the pattern of electrically conductive regions remains;

(iii) coating a second surface of the sheet of electrically conductive material with a layer of resiliently flexible material; and (iv) removing the first layer from the first surface of said sheet.

In this aspect, the method is preferably used to form an electrode array with step (ii) comprising a step of forming a predetermined electrode array pattern in the sheet.

In a preferred embodiment of this aspect, the sheet of electrically conductive material is a biocompatible material. In a preferred embodiment, the sheet is a platinum sheet. The sheet is preferably in the form of a foil having a thickness of between about 1 and 100 microns. The foil preferably has a thickness no greater than 50 microns, more preferably no greater than 20 microns. Other suitable thicknesses can be envisaged. Each sheet can have a dimension of about 50 mm×250 mm. The size of the sheet will though depend on the requirements of the tooling used for the method. As such, sheets of different dimensions can be envisaged.

In a further embodiment, the first layer of electrically conductive material comprises a metal, such as copper. The copper layer is preferably plated to the first surface of the sheet in a plating bath. Prior to the first layer being applied to the sheet, the sheet is preferably supported in a holder. An adhesive such as a spray adhesive or tape adhesive can be used to support the sheet to the holding member. The copper layer can have a thickness of about 100 microns. In another embodiment, the first layer can comprise a layer of electrically conductive paint or electrodisbonding glue applied to the first surface of the sheet. In still a further embodiment the first layer could be formed from any type of conductive removable layer, such as electrically conductive double sided tape.

In a still further embodiment, a thin layer of a suitable conductive material that is biocompatible, such as gold, may be deposited as an interface layer between said first layer and the first surface of the sheet. The thickness of the thin interface layer is preferably substantially smaller than the thickness of the first layer. In one embodiment, the thickness of the first layer and the sheet can be substantially similar or the same.

Once the first layer has been applied to the sheet, it is preferably polished. The purpose of the polishing is to ensure that the first, preferably copper, layer is as flat as possible.

Step (ii) of this aspect preferably comprises a process of using electrical discharge machining (EDM), which is also known as spark erosion, to remove unwanted portions of the sheet. In a preferred embodiment, the EDM equipment used in the process has a cutting tool comprising an electrode. The cutting tool does not physically cut the sheet but instead relies on the equipment generating a series of electrical discharges between the electrode and the sheet in a dielectric fluid. The electrical discharges serve to vaporise the sheet in the region adjacent the cutting tool.

In a preferred embodiment, the cutting tool has a size and shape that matches the size and shape of the portion of the sheet to be removed from the sheet during the machining steps comprising step (ii). In this embodiment, it is preferred that the tool is brought adjacent the sheet at a number of different locations so as to remove differing portions of the sheet. This multiple use of the tool preferably serves to gradually build up the pattern of the electrode array.

In a preferred embodiment, the cutting tool is preferably used to form a linear array of discrete substantially rectangular stimulating pads or electrodes in the sheet, each pad preferably having a conducting portion extending away therefrom to a location distal the pad. Each conducting portion can extend lineally away from its pad. The linear conducting portions are preferably aligned in a parallel arrangement. The conducting portions are hereinafter referred to as "wires" as they serve to provide electrical conduction between each pad to a location distal the electrode array eventually formed using the method defined herein.

Each pad formed in the sheet can have a size of about 0.4 mm$^2$–0.5 mm$^2$. In one embodiment, each electrode can have dimensions of about 500×600 microns. It will be appreciated that the pads of the array can all be the same size. In another embodiment, the dimensions of at least some of the pads can vary from that of others in the array.

In a preferred embodiment, the EDM/milling equipment is used to remove the platinum where desired and at least a portion of the copper layer preferably plated therebeneath. The EDM/milling equipment is preferably operated so as to not punch through the copper layer. The copper layer, as well as enabling the machining to occur, also acts as a carrier of the pattern after the EDM/milling process has occurred, so that the pattern is in a form that is easily handled.

In another embodiment, step (ii) can comprise a step of using laser ablation, micro-knifing, etching, or milling to remove unwanted portions of the sheet. The present inventors have determined that a milling machine having a 100 micron cutter can be used to create wires having a width of between 5 and 50 microns, with a spacing between the wires of about 110 microns.

In a preferred embodiment, step (iii) can comprise coating the second surface with a layer of parylene and/or silicone. The process can further comprise an additional step prior to step (iii) in which at least the second surface of the sheet is cleaned and/or degreased.

The resilient flexible coating can be sprayed on to the second surface of the sheet. Other coating techniques that could be used in step (iii) comprise spinning, dipping, adhering or plasma treatment.

The resiliently flexible layer serves to hold the sheet in the pattern formed during step (ii) during subsequent processing steps. The layer is also preferably relatively electrically insulating and is used as an insulating layer in the electrode array once formed, as is described in more detail below.

Prior to the coating of the second surface with the layer of resiliently flexible material, the method can comprise an additional step in which the areas of sheet removed in step (ii) are filled with a relatively electrically insulating material. The filler can be selected from the group comprising PVA, PEG, and a similar compound. The filler serves to prevent the layer of resiliently flexible material flowing into the gaps in the sheet formed by the removal of those portions of the sheet in step (ii).

The nature of step (iv) will depend on the material used to form the first layer. In one embodiment, the copper layer can be removed by dissolution. In one embodiment, an electromechanical dissolution can be used which operates on the principle that the copper layer can be oxidised and hence dissolved at a potential that is lower than the potential required to oxidise the remaining platinum of the sheet. Where an interface layer, such as a gold layer, is present, the copper layer could be removed by dissolution and the interface layer by electrodissolution.

Following step (iv) of this aspect, the method further preferably comprises the following step:

(v) coating the exposed first surface of the sheet with a layer of resiliently flexible material.

In one embodiment, the layer of material coated to the sheet in step (v) can comprise the same material coated to the second surface in step (iii) as defined herein. In another embodiment, the layer can be a different material.

During step (v), the pads formed in step (ii) can be masked to ensure they remain uncovered with the layer of resiliently flexible material. The wires are preferably not masked and are preferably coated by this layer of resiliently flexible material. In another embodiment, the layer coated to the sheet in step (v) can be removed where necessary, such as by laser ablation, so as to expose the covered pads.

Following step (v), the sheet is preferably trimmed to remove the remaining portions of the sheet that are not comprising the desired electrode array and wires extending therefrom. In one embodiment, the sheet can be trimmed with a knife. In another embodiment, a stamping press can be used to cut the electrode array and wires from the remaining portions of the original sheet. In another embodiment, a mask can be used to mask those portions of the sheet between the arrays prior to a spraying of the silicone through the mask and onto the surface of the sheet.

In a preferred embodiment, all of the required number of pads for a single electrode array are formed in different regions of a single platinum sheet. In this embodiment, each sheet can have a number of respective sets of portions of what will become a single electrode array formed therein. Once each of the sets are formed as described herein, each trimmed set can be stacked one above the other to form an aligned array of stimulating pads.

In one embodiment, the electrode array can comprise 30 stimulating pads. In this embodiment, the formed electrode array can comprise 5 different sets of pads that have been formed in the manner described herein and then stacked to form a single electrode array. In one embodiment, where the electrode array comprises 30 pads, the array can comprise 3 sets of 7 pads, 1 set of five pads and 1 set of 4 pads. In this embodiment, the 3 sets of 7 pads are stacked one on top of the other, the set of five pads is stacked on these sets, with the set of 4 pads on top of the stack. Other combinations of sets can, however, be envisaged.

While the sets of stimulating pads are stacked one upon the other, it will be appreciated that the actual position of the pads in each set are not necessarily vertically aligned. Rather, the set immediately above its lower set may be laterally offset so as to ensure the pads are visible from beneath the stack.

The wires extending from each stimulating pad are preferably of the same length. It can, however, be envisaged that the wires could be formed with different lengths to account for the ultimate offset present when forming the stack and to allow for alignment to an adjoining component of a device, if necessary.

Once the stack is formed, the hitherto at least substantially planar pads are preferably deformed so as to at least partially extend through a third dimension. In a preferred embodiment, each of the stimulating pads are curved out of the plane of the wires for each set of pads. The curvature can be substantially semi-circular. A mandrel can be used to form the curvature in the pads.

Once the stimulating pads have been deformed to have a substantially semi-circular curvature, each of the stimulating pads can be further folded about a longitudinal axis of the array. This folding of the pads preferably serves to bend the pads around the wires of the array. The pads can be folded individually, in small groups, or all together. In one embodiment, the stimulating pads are folded so as to define a lumen that extends through the array.

Once the electrode array is complete it can be encapsulated in a further layer of a biocompatible material to form a electrode carrier member. In a preferred embodiment, the biocompatible material can be a silicone, such as a flexible silicone elastomer-Silastic. Silastic MDX 4-4210 is an example of one suitable silicone for use in the formation of the carrier member. In another embodiment, the elongate carrier member can be formed from a polyurethane or similar material.

In one embodiment, this step can be formed in a mould with the biocompatible material allowed to set around the array. In this embodiment, the stimulating pads are preferably positioned in the mould so as to not be coated with the biocompatible material. In one embodiment, the carrier member can be moulded in a straight configuration. In another embodiment, the carrier member can be moulded in a curved configuration, such as a spirally-curved configuration.

In a further embodiment of the method, step (i) can include a step of also coating the second surface of the sheet with a top layer of said another electrically conductive material. In this embodiment, the top layer on the second surface is preferably thinner than the layer on the first surface. During step (ii), and in particular electrical discharge machining of the sheet, the top layer preferably serves to minimise pitting in the sheet. It is desirable to minimise such pitting as the pits may act as stress risers in the ultimately formed electrode array. The top layer again preferably comprises a layer of copper. The coating can be formed using any one of the methods defined above for coating the first surface of the sheet.

Where the top layer has been coated on the second surface in step (i), it is necessary that this be removed prior to the laying down of the layer of resiliently flexible material on the second surface in step (iii). Where the top layer is thinner, the top layer can be removed by dissolution. The time of dissolution would need to be set to ensure removal of the top layer but not total removal of the layer on the first surface of the sheet. In another embodiment, the layer on the first surface could be masked while the top layer is dissolved. The mask could comprise a double-sided tape or a plastics coating which serves to protect this layer while the top layer is being dissolved.

According to a still further aspect, the present invention is directed to a further invention comprising a method of forming a device comprised of a predetermined pattern of relatively electrically conductive regions and relatively electrically resistive regions, the method comprising the steps of:

(i) coating at least a first surface of an electrically conductive material with a first layer of another material that is relatively electrically insulating;

(ii) forming a predetermined pattern in the sheet of electrically conductive material by removing portions of the sheet therefrom such that at least the pattern of electrically conductive regions remain; and (iii) coating a second surface of the sheet of electrically conductive material with a layer of resiliently flexible material.

In this aspect, the device is preferably an electrode array and step (ii) comprises forming a predetermined electrode array pattern in the sheet.

In this aspect, step (ii) could not comprise use of EDM as described above. Rather, step (ii) could comprise use of a sheet portion removal technique such as laser cutting, microknifing, chemical etching, stamping, milling or roller cutting.

In this aspect, the first layer can comprise a polymeric material, such as a polycarbonate, polytetrafluoroethylene, polyimide, PAA, or PVA, or other dissoluble material.

In this aspect, step (iii) can be performed in a manner similar or identical to that defined above in the preceding aspect.

Still further, this aspect can comprise the following step:

(iv) removing the first layer from the first surface of said sheet.

In another embodiment, the first layer can be retained on the first surface of the sheet and incorporated into the electrode array.

The method of this further aspect can incorporate the steps outlined above with respect to the preceding aspect, where compatible with the steps of the further aspect.

According to a still further aspect aspect, the present application is directed to yet another invention comprising an electrode array formed by the methods defined herein.

In still yet a further aspect, the present invention is an electrode array for use in a tissue stimulating device, the electrode array comprising a plurality of electrodes or stimulating pads, each electrode or pad having at least one electrical conduction means extending away therefrom, the electrodes and electrical conduction means formed from a worked sheet of electrically conducting material.

In a preferred embodiment of this aspect, the sheet is a sheet of platinum, such as is defined above. The at least one electrical conduction means and its respective stimulating pad can be integrally formed. In another embodiment, the at least one electrical conduction means and a stimulating pad can be separately formed and later brought into electrical engagement with each other.

In a preferred embodiment, the stimulating pads and at least a portion of the electrical conduction means are housed within an elongate carrier. In one embodiment, the elongate carrier can be formed from a biocompatible polymeric or elastomeric material. In one embodiment, the elastomeric material can be a silicone rubber. In another embodiment, the elongate member can be formed from a biocompatible polyurethane or similar material. The carrier preferably has a proximal end, a distal end and at least an inner surface adapted to conform to the inner wall of the cochlea. The carrier can be formed from more than one layer.

The electrode array is preferably adapted to receive stimulation signals and transmit electrical stimulations through the stimulating pads to the implantee's auditory nerves.

In a still further embodiment, at least one pad in the array has a surface that is at least adjacent the inner surface of the carrier. More preferably, each of the pads in the array has a surface that is adjacent the inner surface of the elongate carrier. In a further embodiment, the surfaces of the pads are aligned with the inner surface of the elongate member. In another embodiment, the surfaces of the pads stand proud of the inner surface of the elongate carrier. It is also envisaged that the pad surface could also be recessed into the inner surface of the elongate carrier.

The surfaces of the elongate member are preferably smooth to prevent any damage to the cochlea as the array is placed in the cochlea.

The electrode array fabricated by said method will preferably have a straight array and may or may not require further coating with nonconductive materials (e.g. silicone). If a different final shape of the electrode array is required, at least another coating of the array with a nonconductive biocompatible material may be required to create the required shape. In one embodiment, the array is overmoulded to create a curly shaped array.

In yet a further embodiment, a longitudinal lumen can extend through the elongate member for at least a portion of its length. The lumen can act as a substance delivery means for delivering a bio-active substance to the implant site following implantation. In another embodiment, the lumen can receive a stylet to assist in insertion and placement of the array in the cochlea.

In a preferred embodiment, the electrode array is for use as an implantable tissue-stimulating device. More preferably, the tissue-stimulating device is a cochlear electrode assembly, more preferably an intracochlear electrode assembly.

In a preferred embodiment, the intracochlear electrode assembly is a part of an implanted component of a cochlear implant system. The implanted component further preferably comprises a receiver coil and a housing for a stimulator means. The carrier member preferably extends outwardly from the housing of the stimulator means.

In a further embodiment, the carrier member has a leading end that is insertable into a cochlea of an implantee and a trailing end distal the leading end. The wires of the electrode array preferably extend back towards the trailing end of the carrier member.

The wires preferably extend back to the housing to at least a first feedthrough in the wall of the housing. The wires are preferably exposed at or adjacent the trailing end to allow connection to the feedthroughs. In one embodiment, the feedthrough provides hermetic and insulated electrical connection for each wire extending from the electrode assembly into the housing of the implantable component. Each feedthrough can be formed using the method described in U.S. Pat. No. 5,046,242, the contents of which are incorporated herein by reference.

In a preferred embodiment, the orientation of the carrier member as it is firstly inserted through a cochleostomy into the cochlea is preferably substantially straight. More preferably, the implantable orientation is straight. Following completion of implantation, the carrier member preferably adopts a spirally curved configuration that matches the spiral nature of the scala tympani of the human cochlea. The carrier member is preferably pre-formed with this spiral configuration and is then straightened either during manufacture and packaging of the device or prior to implantation. The carrier member is preferably held straight prior to a at least during the initial stages of implantation by a stylet. The stylet preferably extends through a lumen of the carrier member such as the lumen described herein that is formed by the folding of the electrodes about the wires.

In a further embodiment, the housing is preferably implantable in a recess of the temporal bone adjacent the ear of the implantee that is receiving the output of the implant system. The housing is preferably formed from a biocompatible material or has a biocompatible coating. The housing can be coated with a layer of silicone or parylene.

As already discussed, the implantable component preferably also comprises a receiver coil. The receiver coil preferably comprises a wire antenna coil. The antenna coil can be comprised of at least one, and preferably at least three, turns of electrically insulated platinum or gold wire tuned to parallel resonance by a capacitor internal to the housing. The electrical insulation of the antenna coil can be provided by a flexible silicone moulding and/or silicone or polyurethane tubing. The external coil can be constructed in a similar fashion to the implanted coil or have a different construction.

The antenna coil is preferably external of the housing. Electrical connection between the antenna coil and componentry of the implantable componentry within the housing can be provided by two hermetic and electrically insulated ceramic feedthroughs or an electrical conductor. The ceramic feedthroughs can be formed using the method described in abovementioned U.S. Pat. No. 5,046,242.

The antenna coil of the implantable component preferably acts as part of the radio frequency (RF) link to allow transcutaneous bidirectional data transfer between the implantable component and an external components of the cochlear implant system. The radio frequency signals can comprise frequency modulated (FM) signals. While described as a receiver coil, the receiver coil can preferably transmit signals to the transmitter coil which receives the signals.

The link between the two coils also provides a means of powering the componentry of the internal component. Where the implantable component further has an on-board or implantable power source, such as a rechargeable battery, the link can provide a means of inductively charging the battery when required.

The implanted housing preferably contains, in addition to the stimulator means, a receiver means. The receiver means is preferably adapted to receive signals from the external component.

The housing of the external component preferably houses a speech processor adapted to receive signals output by a microphone. In a preferred embodiment, the microphone can be mounted to the housing or an ear hook member. Other suitable locations for the microphone and/or the housing for the speech processor can be envisaged, such as a lapel of the implantee's clothing.

The speech processor encodes the sound detected by the microphone into a sequence of electrical stimuli following given algorithms, such as algorithms already developed for cochlear implant systems. The encoded sequence is transferred to the implanted receiver/stimulator means using the transmitter and receiver coils. The implanted receiver/stimulator means demodulates the FM signals and allocates the electrical pulses to the appropriate attached electrode by an algorithm which is consistent with the chosen speech coding strategy.

The external component preferably further comprises a power supply. The power supply can comprise one or more rechargeable batteries. The transmitter and receiver coils are used to provide power via transcutaneous induction to the implanted stimulator/receiver means and the electrode array.

While the implant system can rely on external componentry, in another embodiment, the microphone, speech processor and power supply can also be implantable. In this embodiment, these components can be contained within a hermetically sealed housing or the housing used for the stimulator means.

In this aspect, the array can be formed by the embossing or EDM processes defined herein.

In a still further aspect, the present invention is a device having an electrically conductive component, the component being formed from a worked sheet of electrically conducting material, the sheet having a thickness less than about 50 microns.

In this aspect, the sheet can be a platinum foil, such as is defined herein. For example, the platinum foil can have a thickness no greater than about 20 microns. The sheet can further have a dimension of about 50 mm×250 mm.

In a further embodiment of this aspect, the electrically conductive component can comprise at least one conductive wire formed from the platinum foil, the wire having a width of between about 1 and 100 microns, more preferably 1 and 70 microns.

Still further, the electrically conductive component can comprise a plurality of discrete conductive wires formed from the platinum foil, each wire being electrically insulated from its neighbouring wire. In one embodiment, the spacing between neighbouring wires can be between about 10 and 100 microns. Still further, the wires can be disposed for at least a portion of their lengths in a parallel arrangement.

Each conductive wire can extend from an electrode also formed from the platinum foil. The electrode can have an areal dimension of less than about 0.5 mm$^2$.

In this aspect, the device can be a component of a tissue stimulating device, such as an intracochlear electrode assembly. In another embodiment, the device can be a biosensor. Still further, the device can be a miniature wire.

In this aspect, the component can be formed by machining the sheet of electrically conductive material to remove a portion therefrom such that at least a pattern of electrically conductive regions remains. The machining of the sheet can comprise a step of using electrical discharge machining (EDM) to remove unwanted portions of the sheet. Other methods as defined herein can also be utilised.

In yet a further aspect, the present invention is a method of forming a device comprised of a predetermined pattern of relatively electrically conductive regions and relatively electrically resistive regions, the method comprising the steps of:

(i) mounting a sheet of electrically conductive material in an electrical discharge machining (EDM) device, the device having a discharge electrode of a predetermined shape;

(ii) programming the EDM device to bring the electrode adjacent the sheet; and (iii) operating the EDM device to remove a portion of the sheet corresponding to the shape of the electrode.

In this aspect, the sheet prior to mounting in the EDM device is firstly coated on at least a first surface thereof with a sheet of electrically conductive material. The layer can comprise a layer of metal, such as copper. The copper layer is preferably plated to the first surface of the sheet in a plating bath. Prior to the first layer being applied to the sheet, the sheet is preferably supported in a holder. An adhesive such as a spray adhesive or tape adhesive can be used to support the sheet to the holding member. The copper layer can have a thickness of about 100 microns. In another embodiment, the first layer can comprise a layer of electrically conductive paint applied to the first surface of the sheet. In still a further embodiment the first layer could be formed from any type of conductive removable layer.

Once the first layer has been applied to the sheet, it is preferably polished. The purpose of the polishing is to ensure that the first, preferably copper, layer is as flat as possible.

Once the pattern has been formed in the sheet, a second surface of the sheet of electrically conductive material can be coated with a layer of resiliently flexible material. Once completed, the method can then comprise a step of removing the first layer from the first surface of said sheet.

In this aspect, the method is preferably used to form an electrode array with step (iii) comprising a step of forming a predetermined electrode array pattern in the sheet.

In a preferred embodiment of this aspect, the sheet of electrically conductive material is a biocompatible material. In a preferred embodiment, the sheet is a platinum sheet. The sheet is preferably in the form of a foil having a thickness of between about 10 and 50 microns. The foil preferably has a thickness no greater than 50 microns, more preferably no greater than 20 microns. Other suitable thicknesses can be envisaged. Each sheet can have a dimension of about 50 mm×250 mm. The size of the sheet will though depend on the requirements of the tooling used for the method. As such, sheets of different dimensions can be envisaged.

Step (iii) of this aspect preferably comprises a process of using electrical discharge machining (EDM), which is also known as spark erosion, to remove unwanted portions of the sheet. In a preferred embodiment, the EDM equipment used in the process has a cutting tool comprising an electrode. The cutting tool does not physically cut the sheet but instead relies on the equipment generating a series of electrical discharges between the electrode and the sheet in a dielectric fluid. The electrical discharges serve to vaporise the sheet in the region adjacent the cutting tool. It is considered that other types of material removal such as those performed by a milling machine could also be implemented in this step to form the desired shapes on the sheet.

In a preferred embodiment, the cutting tool has a size and shape that matches the size and shape of the portion of the sheet to be removed from the sheet during the machining steps comprising step (ii). In this embodiment, it is preferred that the tool is brought adjacent the sheet at a number of different locations so as to remove differing portions of the sheet. This multiple use of the tool preferably serves to gradually build up the pattern of the electrode array.

BRIEF DESCRIPTION OF THE DRAWINGS

By way of example only, preferred embodiments of the invention are now described with reference to the accompanying drawings, in which:

FIG. 15b is a cross-sectional view of a sheet of electrically conductive material mounted to a sheet of biocompatible resiliently flexible material ready to be punched using the punch of FIG. 15a;

FIG. 15c is a cross-sectional view of the sheet of FIG. 15b following use of the punch of FIG. 15a;

FIG. 17b is a plan view of a platinum sheet showing a line of the sheet vaporised through use of the tool depicted in FIG. 17a;

FIG. 17c is a plan view of the platinum sheet of FIG. 17b depicting how an electrode and adjoining wire can be formed following a second use of the tool of FIG. 17a;

FIG. 17d is a plan view of the platinum sheet of FIG. 17b depicting how an array of electrodes and adjoining wires are formed by a plurality of uses of the tool of FIG. 17a;

FIG. 18b is a plan view of a platinum sheet showing how three lines of the sheet are vaporised through use of the tool depicted in FIG. 18a;

FIG. 18c is a plan view of the platinum sheet of FIG. 18b depicting how three electrodes and adjoining wires can be formed following a second use of the tool of FIG. 18a;

FIG. 18d is a plan view of the platinum sheet of FIG. 18b depicting how an array of electrodes and adjoining wires are formed by a plurality of uses of the tool of FIG. 18a;

FIG. 19 is a plan view of a platinum sheet depicting how different sets of electrodes and adjoining wires can be formed in a platinum sheet through appropriate machining;

PREFERRED MODE OF CARRYING OUT THE INVENTION

Figure 16:
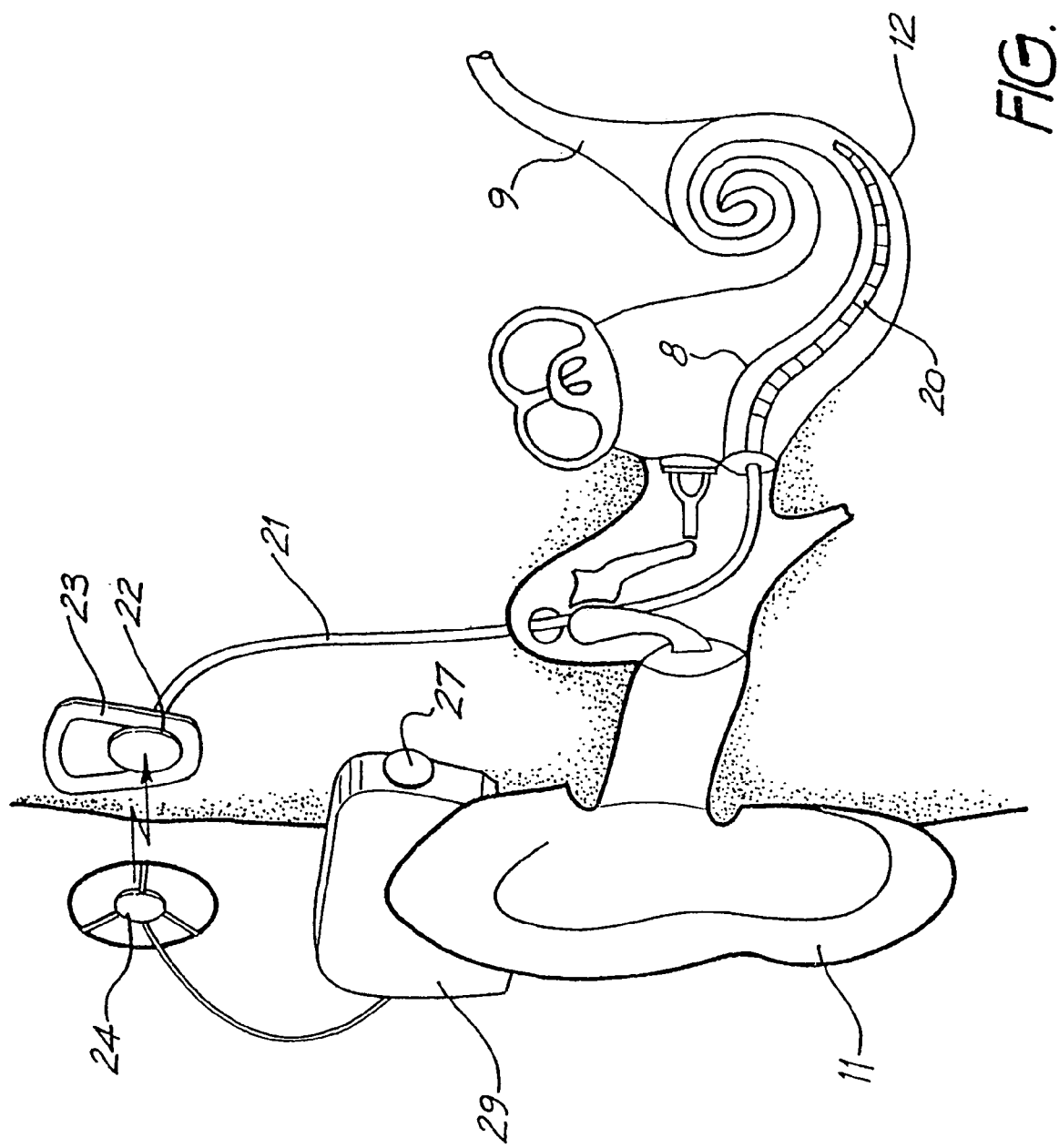
FIG. 16 is a pictorial representation of a prior art cochlear implant system.

Before describing the features of the present invention, it is appropriate to briefly describe the construction of one type of known cochlear implant system with reference to FIG. 16.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

Figure 1:
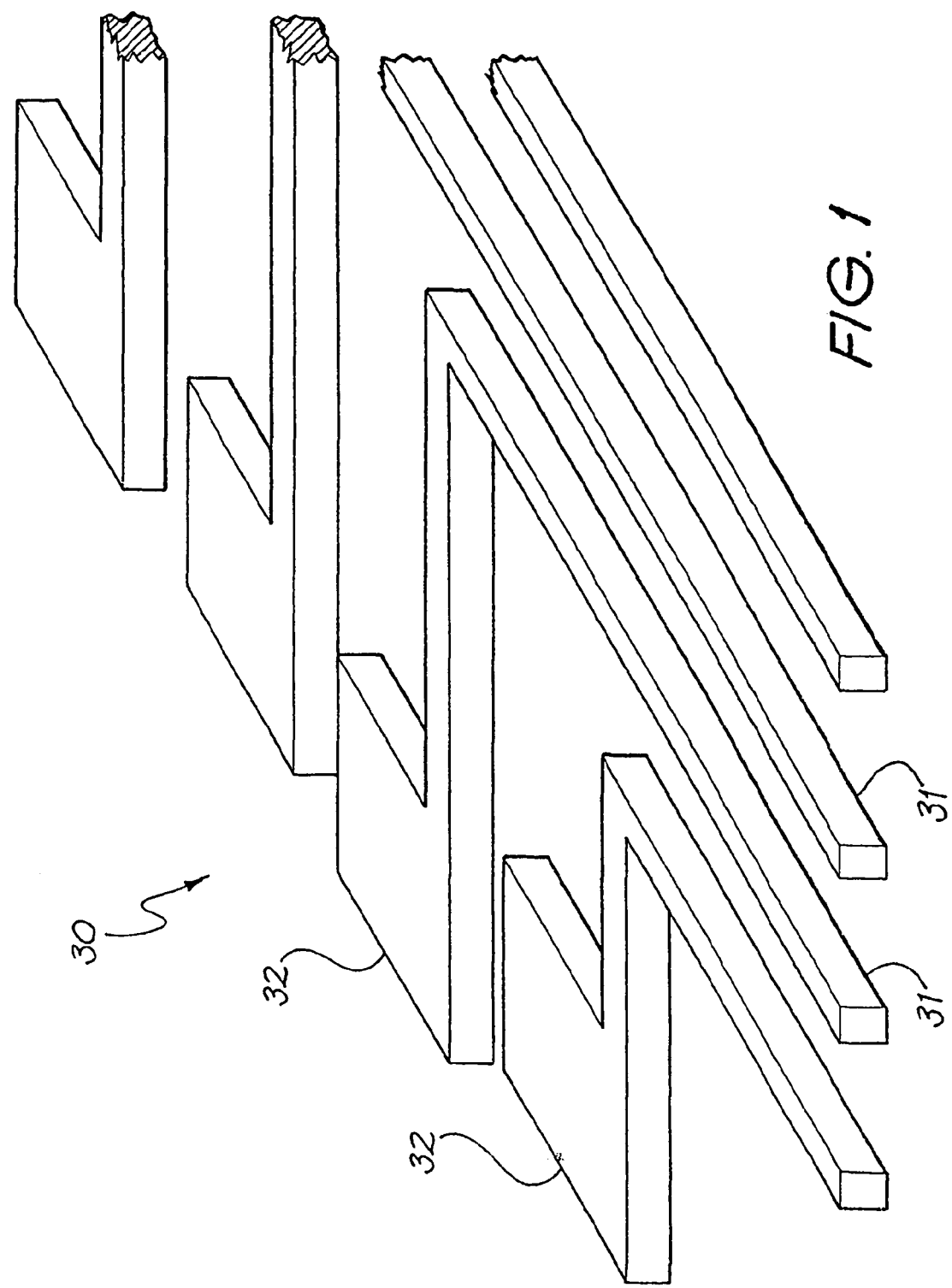
FIG. 1 is a perspective view of one example of the protrusions of an embossing tool for use in one embodiment of the method according to the present invention.

One simplified example of an embossing tool for use in the method of the present invention is depicted generally as 30 in FIG. 1. In the depicted embodiment, the tool 30 is formed from copper, however, other suitable materials can be envisaged. The tool 30 has a plurality of parallel linearly aligned protrusions 31. The widths of each of the protrusions 31 is representative of the desired width of the wires in the final product and is in the vicinity of between about 1 and 100 microns, more preferably 1 and 70 microns. The spacing between neighbouring protrusions can be between about 10 and 100 microns, representative of the spacings between the wires of the final product. Each protrusion 31 has a right angle turn that terminates in a larger electrode-forming protrusion 32. Use of the tool 30 results in the formation of a raised pattern in a suitable sheet of electrically conducting material, such as platinum, that is pressed by the protrusions 31 and electrode-forming protrusions 32.

Once the raised pattern is formed in the platinum sheet, as is described below, those portions of the sheet that are not part of the raised pattern can be removed from the sheet by abrasion or other suitable methods. The result is as plurality of electrodes each having an integrally formed electrical conduction means extending away therefrom.

Figure 2:
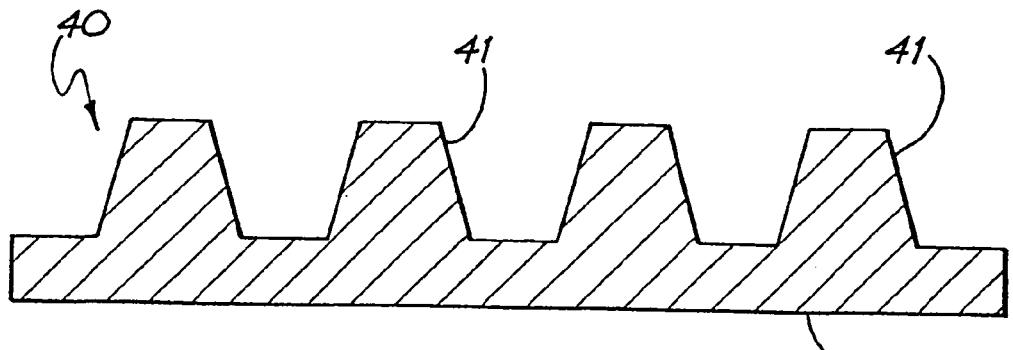
FIG. 2 is a cross-sectional view of another embossing tool for use in the method according to the present invention.

FIG. 2 is a cross-sectional view of a portion of another embossing tool 40, made in this case from copper, for use in the method according to the present invention. The portion depicted in FIG. 2 is of the protrusions 41 used to form the electrical conduction means for the electrode array.

The protrusions 41 extend outwardly from a base 42. The protrusions 41 narrow in thickness from their base to their top. Each protrusion at its base has a thickness of between about 48 and 54 microns. At the top, each protrusion has narrowed in thickness to between about 28 and 30 microns. The distance between adjacent protrusions at the base is between about 65 and 67 microns, while the distance between the protrusions at the top is between about 86 and 87 microns. Each protrusion has a height of about 30 microns. These dimensions should be considered as illustrative only.

Figure 3:
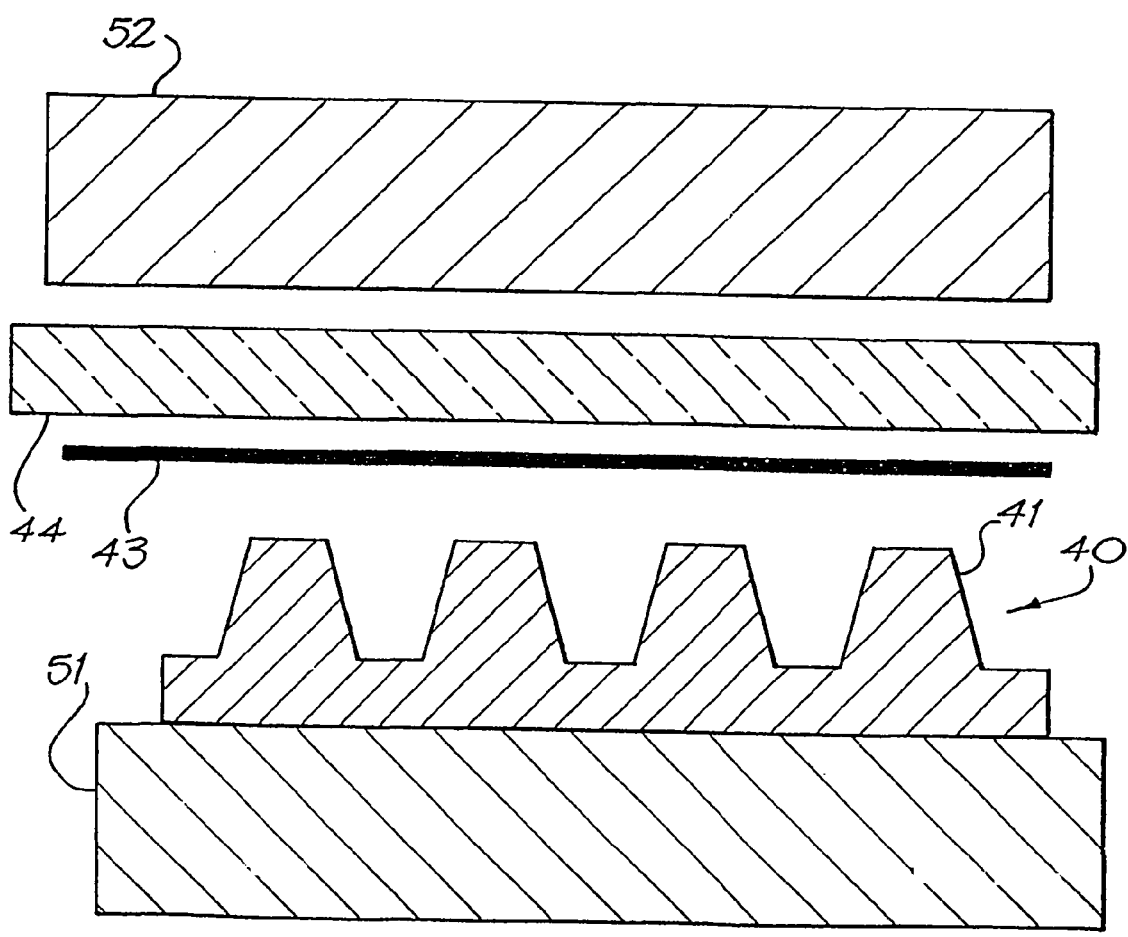
FIG. 3 is an expanded cross-sectional view of the embossing tool of FIG. 2 positioned in a horizontal press.

As depicted in FIG. 3, the tool 40 can be positioned on a relative stationary platen 51 of a press. The press used in the method preferably can apply a pressure of up to 4–5 tonnes. Once the tool 40 is in position, a sheet of platinum 43 (10–15 microns thickness) is placed on the tool 40. A silicone backing layer 44 is then laid over the sheet 43. In another embodiment, a thin layer of a lubricant can be placed between the tool 40 and the sheet of platinum 43 and between the sheet of platinum 43 and the backing layer 44, Once the silicone backing layer 44 is in position, the top platen 52 of the press can be moved relatively downwardly to apply pressure to the sheet 43 positioned on the tool 40. The platen 52 preferably applies an initial pressure for a predetermined period of time (eg. 2 tonnes for 15 seconds) before an increased pressure is applied for a further predetermined period of time (eg. 4 tonnes for 60 seconds).

Once pressed, the platen 52 moves relatively upwardly to allow removal of the tool 40 from the press with the sheet 43 and backing layer 44 still in position on the tool 40.

Figure 4:
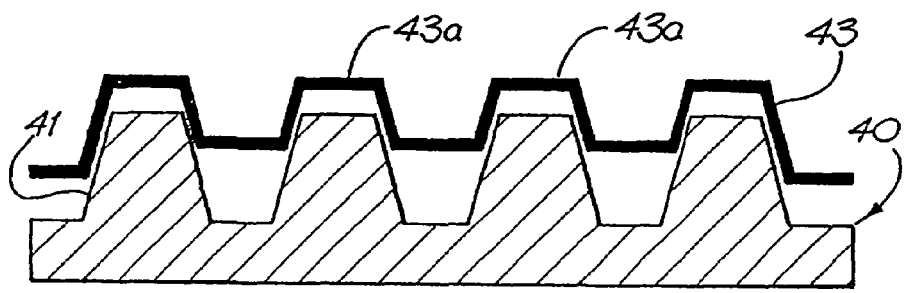
FIG. 4 is an expanded cross-sectional view of an embossed sheet positioned on the embossing tool of FIG. 2.

Once removed from the press, the backing layer 44 can be removed leaving the platinum foil 43, with a plurality of raised ridges formed therein (43a), in position on the tool 40 as depicted in FIG. 4.

Figure 5:
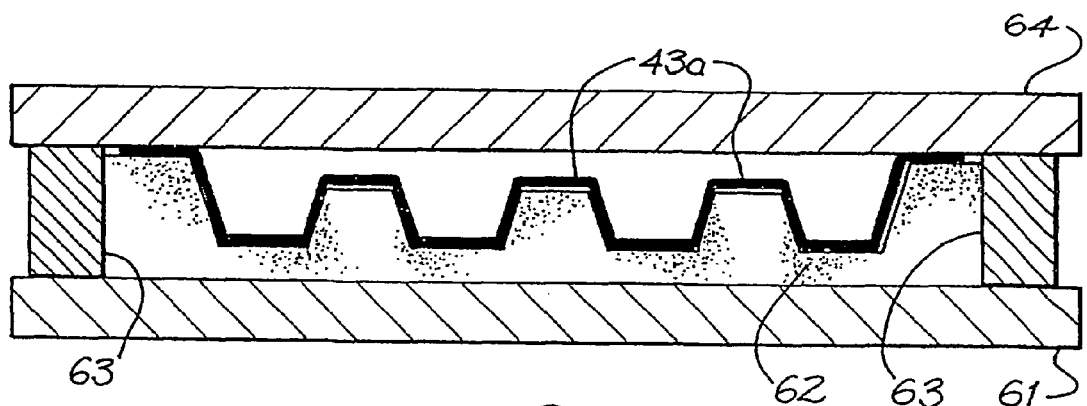
FIG. 5 depicts the embossed sheet being prepared for an abrading step.

FIG. 5 depicts the steps necessary to prepare the embossed sheet 43 for removal of those portions of the sheet 43 that are unwanted. A steel base plate 61 has a relatively thin smear of electrodisbonding adhesive 62 (eg. ElectRelease™ E4 available from EIC Laboratories, Inc.) or other adhesive coated thereon. Spacers 63 having a height of about 80 are placed on the base plate 61 on each side of the adhesive 62. The lower face of the embossed platinum foil 43 is then placed on the glue with the ridges 43a extending upwardly. A top plate 64 is then placed on the top of the embossed foil 43 and pressed down until it rests on the spacers 63.

The embossed foil 43 remains between plates 61 and 64 until the adhesive 62 has cured. Once the adhesive is cured, the top plate 64 and spacers 63 are removed. The support base 61, with the embossed platinum foil sheet 43 adhered thereto, is then ready to undergo step (ii) of the process defined above.

With the raised ridges 43a extending outwardly away from the base plate 61, an abrading means 65 is used to remove a portion of the raised pattern formed in the sheet 43. It will be appreciated that if the foil 43 had been adhered to the base plate 61 with the raised ridges 43a facing downwardly into the adhesive then the non-raised portions of the foil 43 would be removed in the step of the process depicted in FIG. 6.

Figure 6:
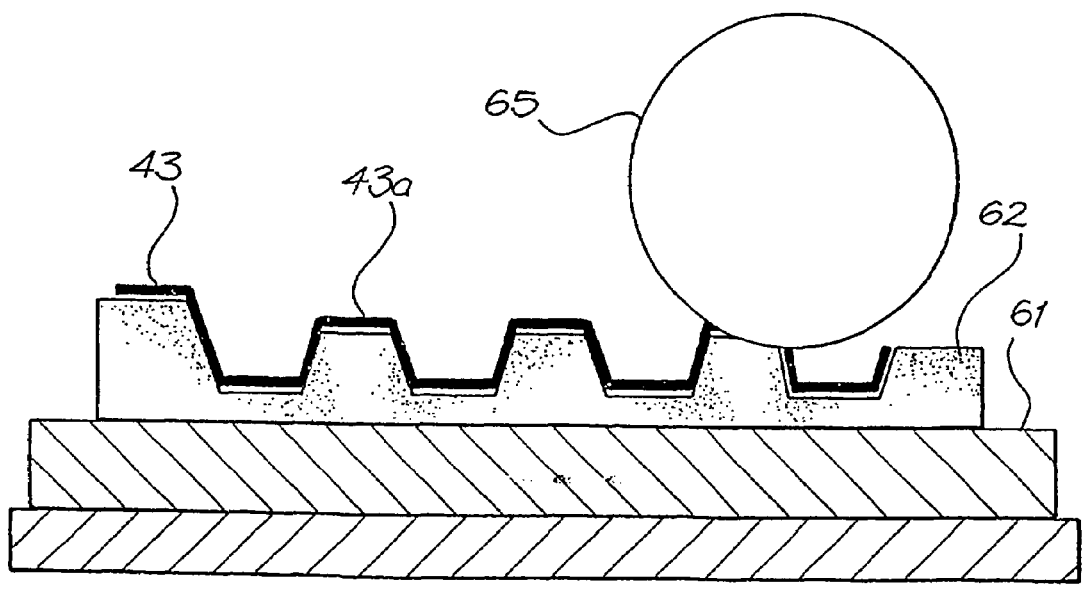
FIG. 6 depicts a portion of the embossments formed in the embossed sheet being removed in an abrading step.
Figure 7:
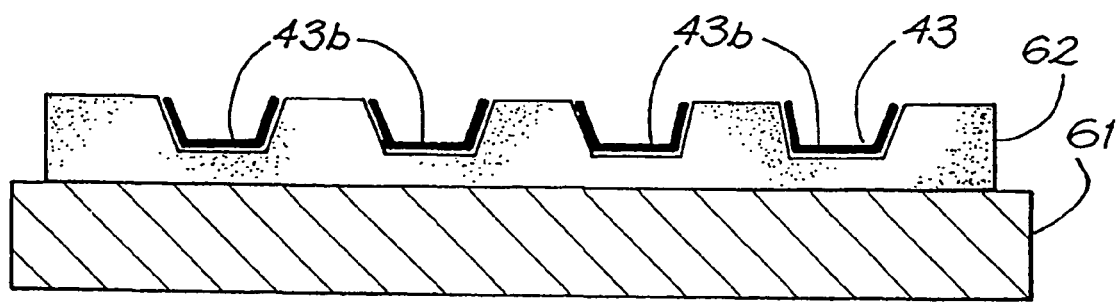
FIG. 7 depicts the sheet following completion of the abrading step.

As is depicted in FIG. 7, the remaining portions 43b of the original sheet 43 left after completion of the step depicted in FIG. 6 preferably comprise a plurality of electrically independent portions. In FIG. 7, the depicted remaining portions 43b represent, in cross-section, longitudinal conduction means that extend to respective electrodes (not depicted) also formed from the sheet 43.

Figure 8:
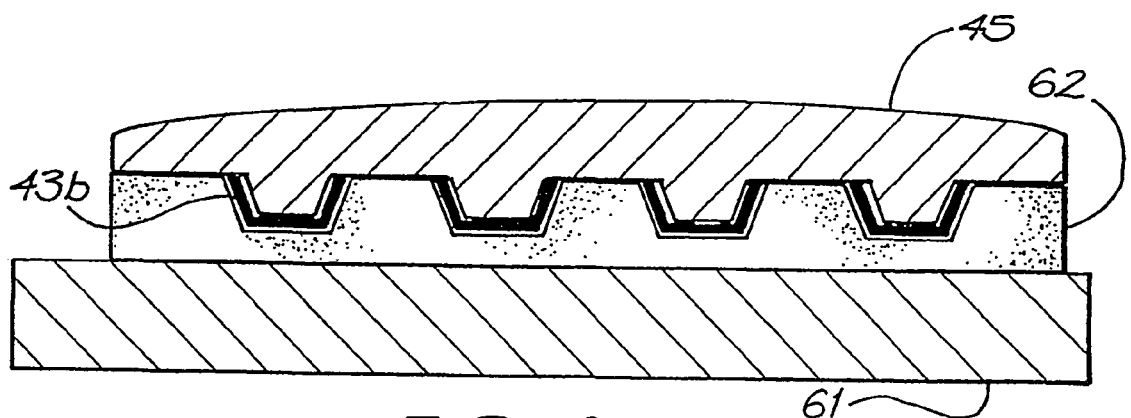
FIG. 8 depicts the sheet following encapsulation with a layer of silicone.

As depicted in FIG. 8, the method further includes the step of encapsulating the embossed sheet 43 in an electrically insulating, biocompatible and resiliently flexible silicone 45.

Once the silicone 45 is cured, an electrical connection can be made to the remaining portions 43b of the platinum and to the base plate 61. The respective electrical connections are then preferably connected to a power supply. The positive terminal of the power supply is preferably connected to the remaining portions 43b and the negative terminal to the base plate 61. Once turned on, the provision of electrical current through the electrodisbonding adhesive 62 results in it releasing from the embossed sheet 43b. The applied voltage is preferably between 5V and 50V for a period of between 1 second and 30 minutes.

Figure 9:
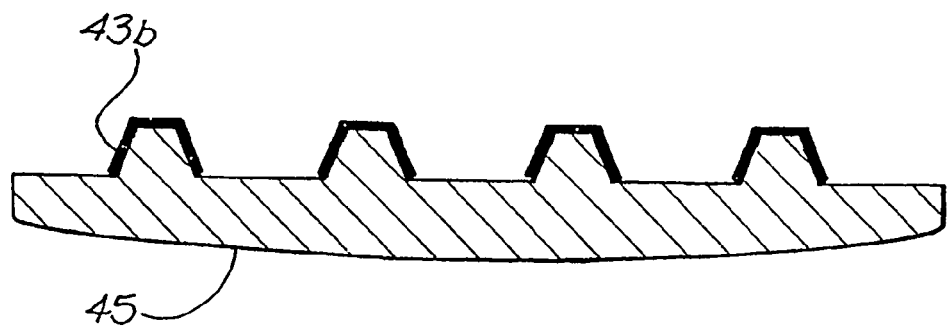
FIG. 9 is a cross-sectional view of the formed electrical conduction means having a silicone encapsulation formed on one side.

Once disbanded, the result is a plurality of separate electrically independent conductive portions 43b having a layer of silicone 45 encapsulated on one side thereof, as depicted in FIG. 9. If desired, the electrode array and electrical conduction means can undergo further processing, including further encapsulating steps, washing and drying, to render it suitable for implantation as an intracochlea electrode assembly.

Figure 10:
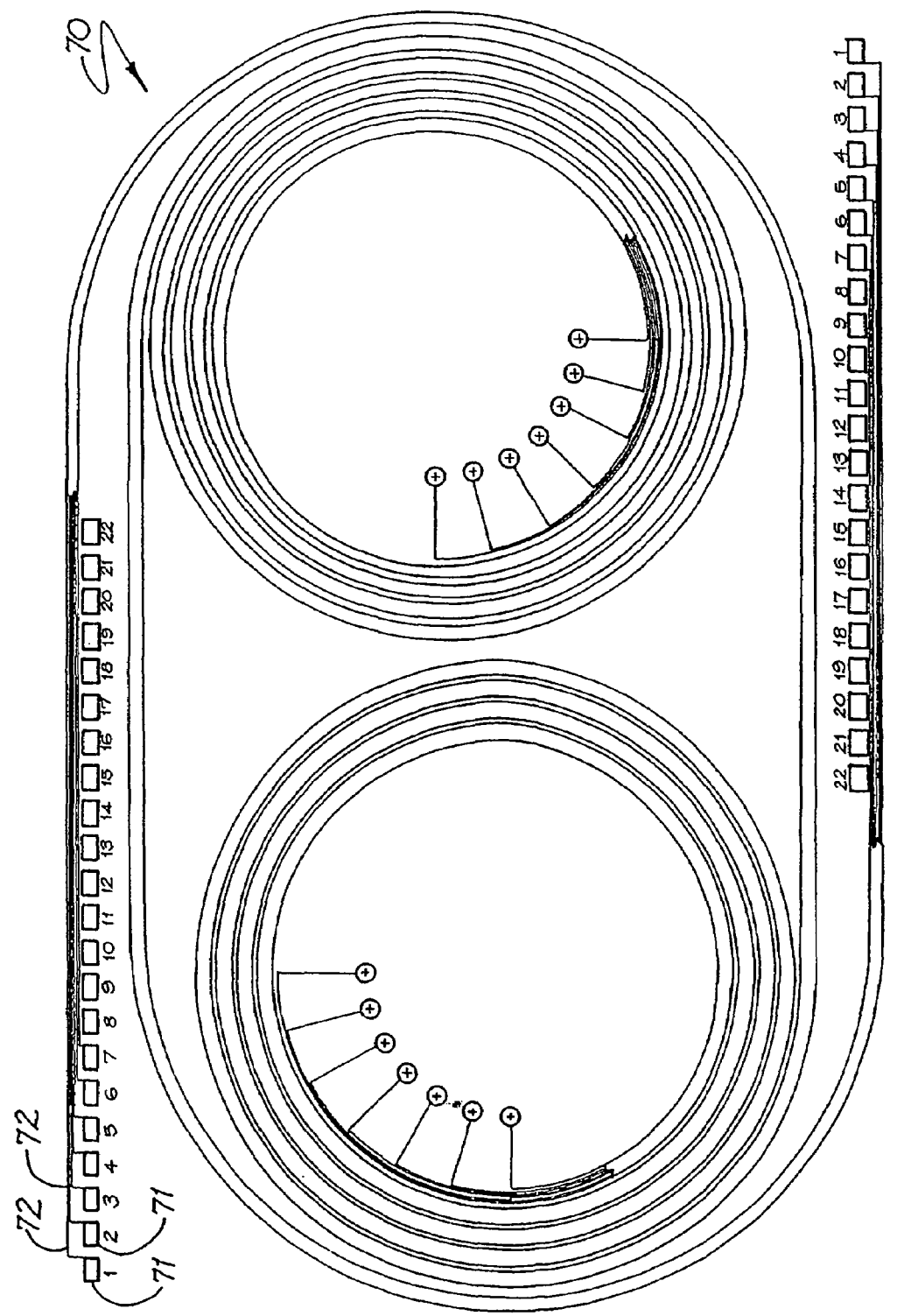
FIG. 10 is a plan view of an embossing tool for use in forming two electrode arrays for a cochlear implant from a single sheet of electrically conducting material.

FIG. 10 is a plan view of the raised pattern formed in an embossing tool 70 for forming two electrode arrays for use as cochlear implant electrode arrays.

The depicted tool 70 is adapted to form suitable embossments in a sheet of platinum foil that are ultimately used to form electrodes 1 to 7 of the cochlear implant electrode array. The remaining formed electrodes are formed by separate tools and laminated together with the electrodes formed by tool 70 to form a complete array.

The tool 70 in addition to having suitable protrusions 71 for forming each of the electrodes 1 to 7 also has linear protrusions 72 extending away from the electrode-forming protrusions 71 that are used to form the respective integral electrical conduction means for each formed electrode.

As depicted, each of the protrusions 72 eventually spiral inwardly in ever decreasing circles. At an end distal the electrode protrusion 71, each protrusion 72 terminates in a feedthrough electrode protrusion 73. The distal protrusion 73 forms an electrode for connection to the feedthrough of a receiver/stimulator means that will preferably be electrically connected to the electrode assembly formed using the tool.

FIGS. 11 to 15 depict a further method of forming an electrode array according to the present invention.

Figure 11:
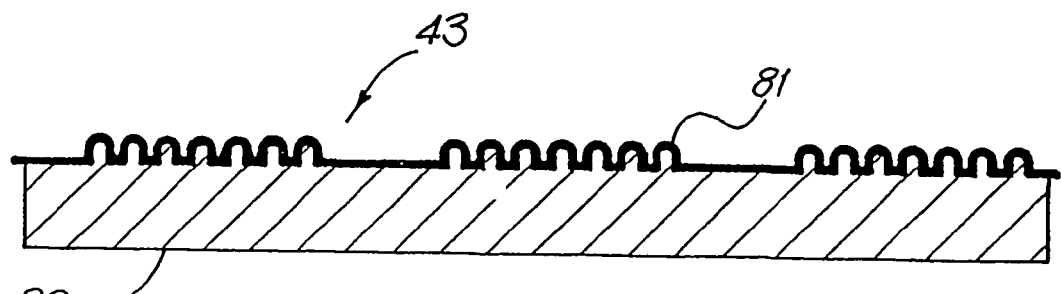
FIG. 11 is an enlarged cross-sectional view of the embossments formed in the sheet of platinum by the protrusions of the embossing tool of FIG. 10 in the region used for formation of the electrical conduction means.

In FIG. 11, the embossing tool 80 is formed from an etched silicon wafer. The tool 80 has three groups of protrusions that result in the formation of an equivalent number of ridges 81 in the platinum foil sheet 43 when pressed by the tool in a manner similar to that depicted in FIG. 3.

Figure 12A:
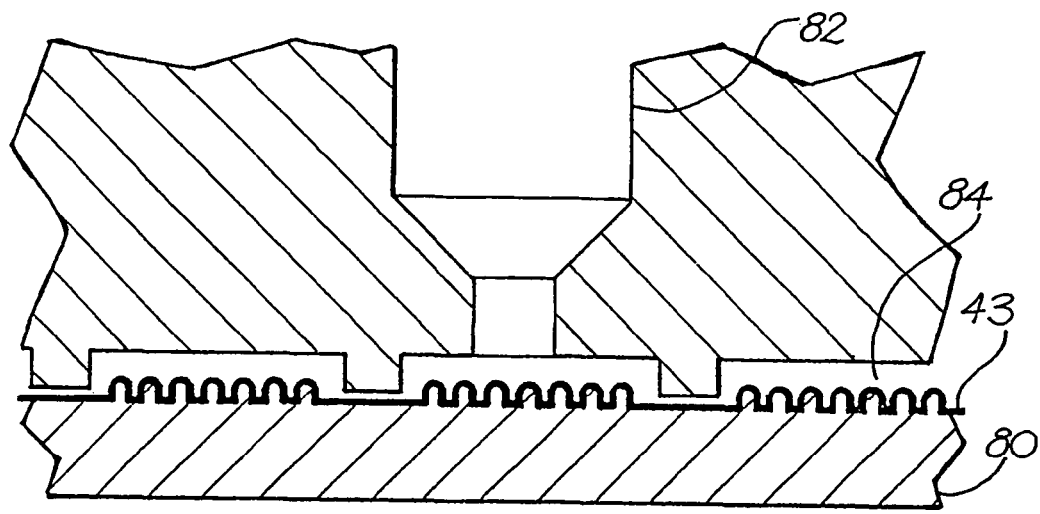
FIGS. 12a, 12b, 13, 14 and 15 are simplified cross-sectional views of further steps of the process for forming an electrode array from a sheet of electrically conducting material according to the present invention.
Figure 12B:
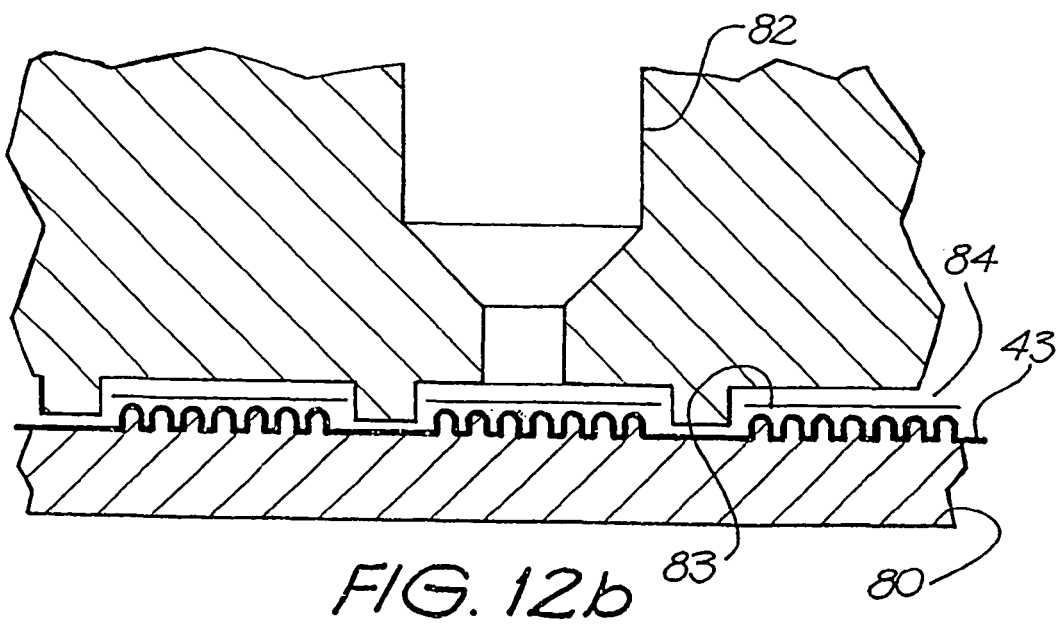

Once pressed, the sheet 43, with the tool 80, still in place can have a thin layer of silicone 84 moulded thereto as depicted in FIG. 12a. The molded layer 84 is preferably relatively thin. During the subsequent process, a keeper 82 is used to hold the molded layer 84 and platinum foil 43 in place. If necessary, more than one layer can be molded or a suitable platinum/silicon adhesive layer 83 can be used to assist in bonding the layer 84 to the sheet 43 (see FIG. 12b).

Figure 13:
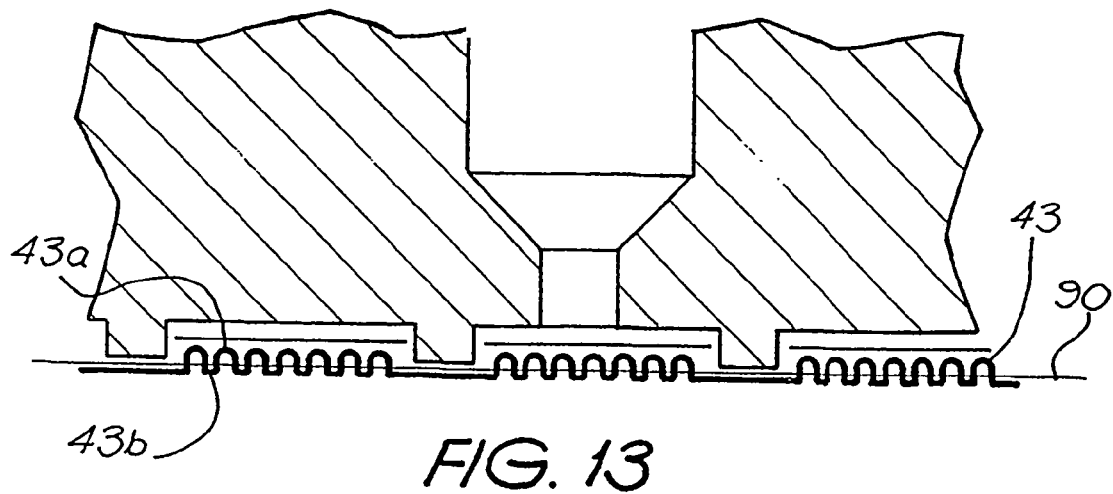

As depicted in FIG. 13, the non-pressed portions 43b are removed from the sheet 43 by an abrading or polishing step. Below polishing line 90, the platinum sheet is removed from sheet 43 so leaving the formed ridges 43a embedded in the silicone layer 84. The depicted ridges 43a are electrically isolated from each other and act as longitudinal conduction means for the formed electrodes as discussed above.

Figure 14:
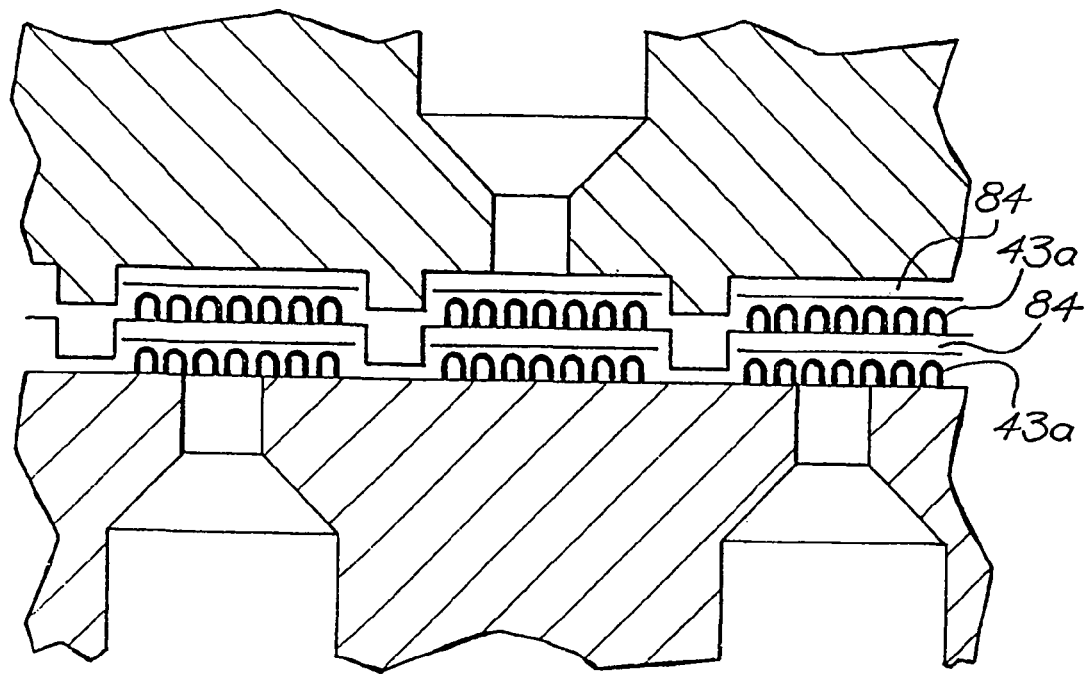

To form a full array of electrodes for a cochlear implant array, three laminations are required of three separately formed smaller electrode arrays. As depicted in FIG. 14, a second set of electrical conduction means are formed and then laid above the first set of electrical conduction means. This process is then again repeated to form the full array.

Figure 15:
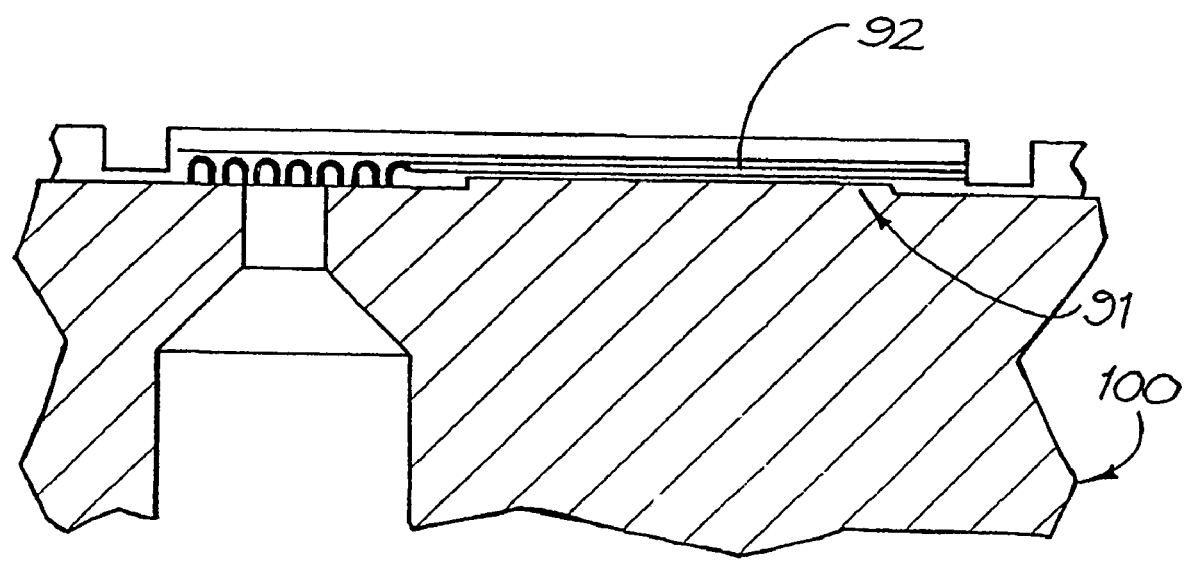

It is preferred during the molding process that the formed electrode pads are recessed slightly into the surrounding silicone. One example of how this can be achieved is depicted in FIG. 15. In FIG. 15, the laminating die 100 includes upstanding insets 91 that extend outwardly from the die 100 and which are aligned with the positions of the formed electrodes 92. These insets 91 preferably abut the electrodes 92 and so prevent the encapsulation covering the electrodes 92 during the subsequent encapsulating process.

Figure 15A:
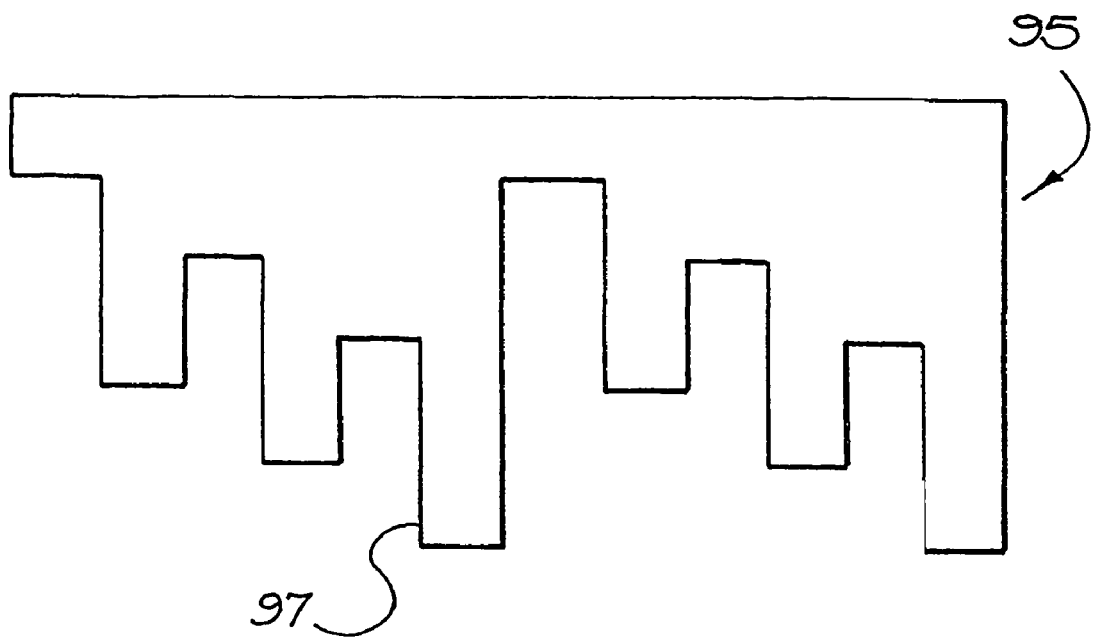
FIG. 15a is a cross-sectional view of a punch for use in another embodiment of an invention according to the present application.
Figure 15B:
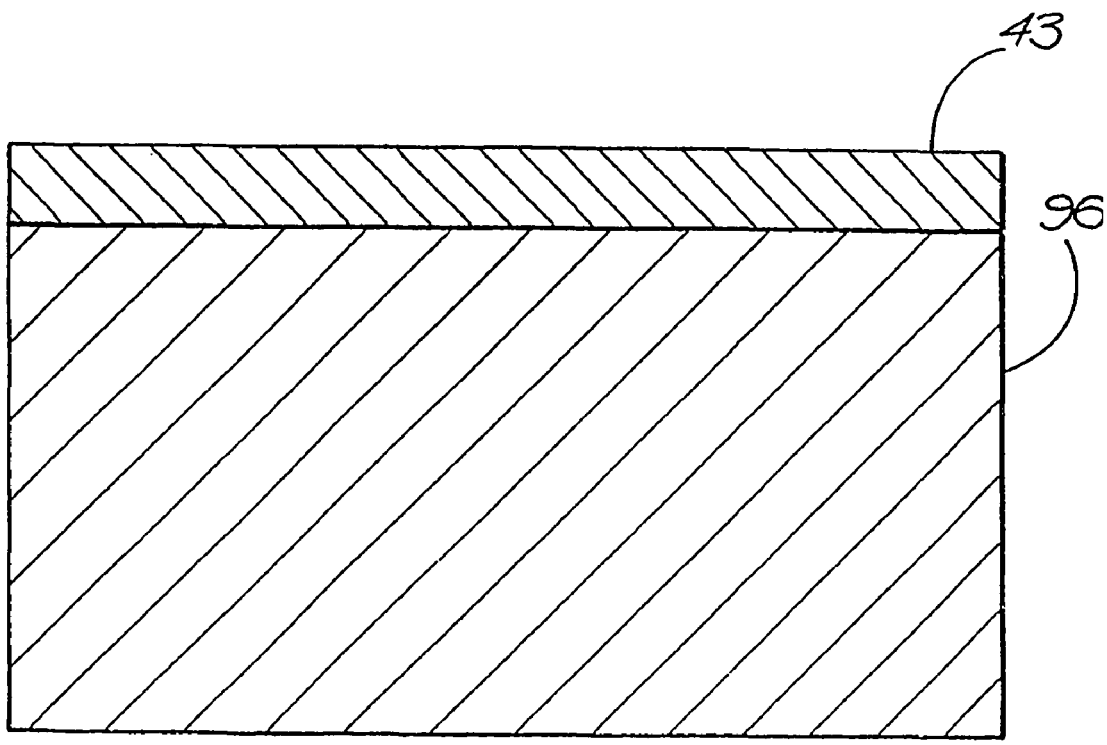
Figure 15C:
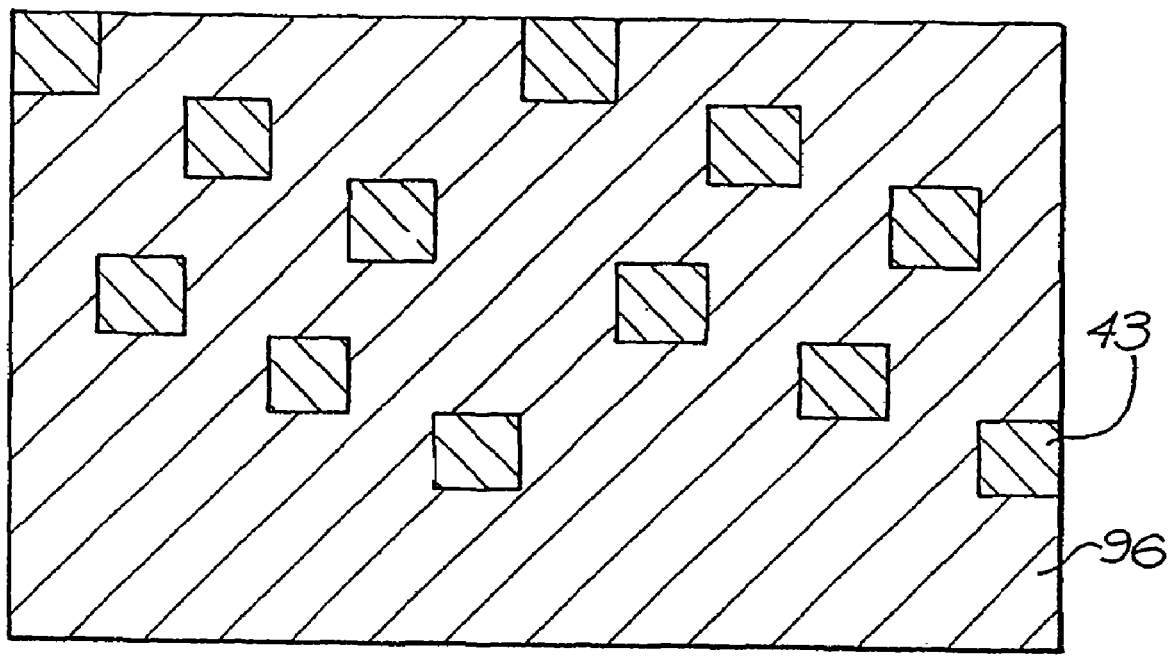

FIG. 15a depicts an alternative device for use in the working of a sheet of electrically conductive material, such as platinum foil as already described herein. The device comprises a punch tool 95 that is adapted to be moved relative to a sheet 96, such as that depicted in FIG. 15b. The sheet of FIG. 15b comprises a layer of platinum foil 43 that has been mounted to a surface of a thicker layer of silicone 96.

In the depicted example, on relative downward movement of the punch 95, its working surface 97 serves to effectively slice or cut portions of the platinum from the sheet 43 and drive them to varying depths within the silicone layer 96. Due to the resilient nature of the silicone, the silicone layer can be expected to at least substantially close about the punched portions of the sheet 43 on relative upward withdrawal of the punch 95.

In the depicted example, the punch preferably extends longitudinally such that during use longitudinal portions of platinum sheet are forced into the silicone layer. This longitudinal portions can then act as conducting wires as has been described herein.

The depicted process described above results in the formation of a plurality of electrode pads and integrally formed electrical conduction means embedded within a silicone carrier. The process is relatively straightforward and has the potential to be automated so reducing the cost of manufacture of electrode arrays for devices such as cochlear implants.

An alternative process for the manufacture of an electrode array is depicted in FIGS. 17a to 24.

Current techniques for the manufacture of electrode arrays for cochlear implant systems are highly labour intensive. This is in the main due to the intricate nature of the array and the very small dimensions of the array necessary to allow it to be inserted in the scala tympani of the human cochlea. Being an implantable device, the method of manufacture also needs to result in a biocompatible product that is not susceptible to damage from long-term placement in the body.

Figure 24:
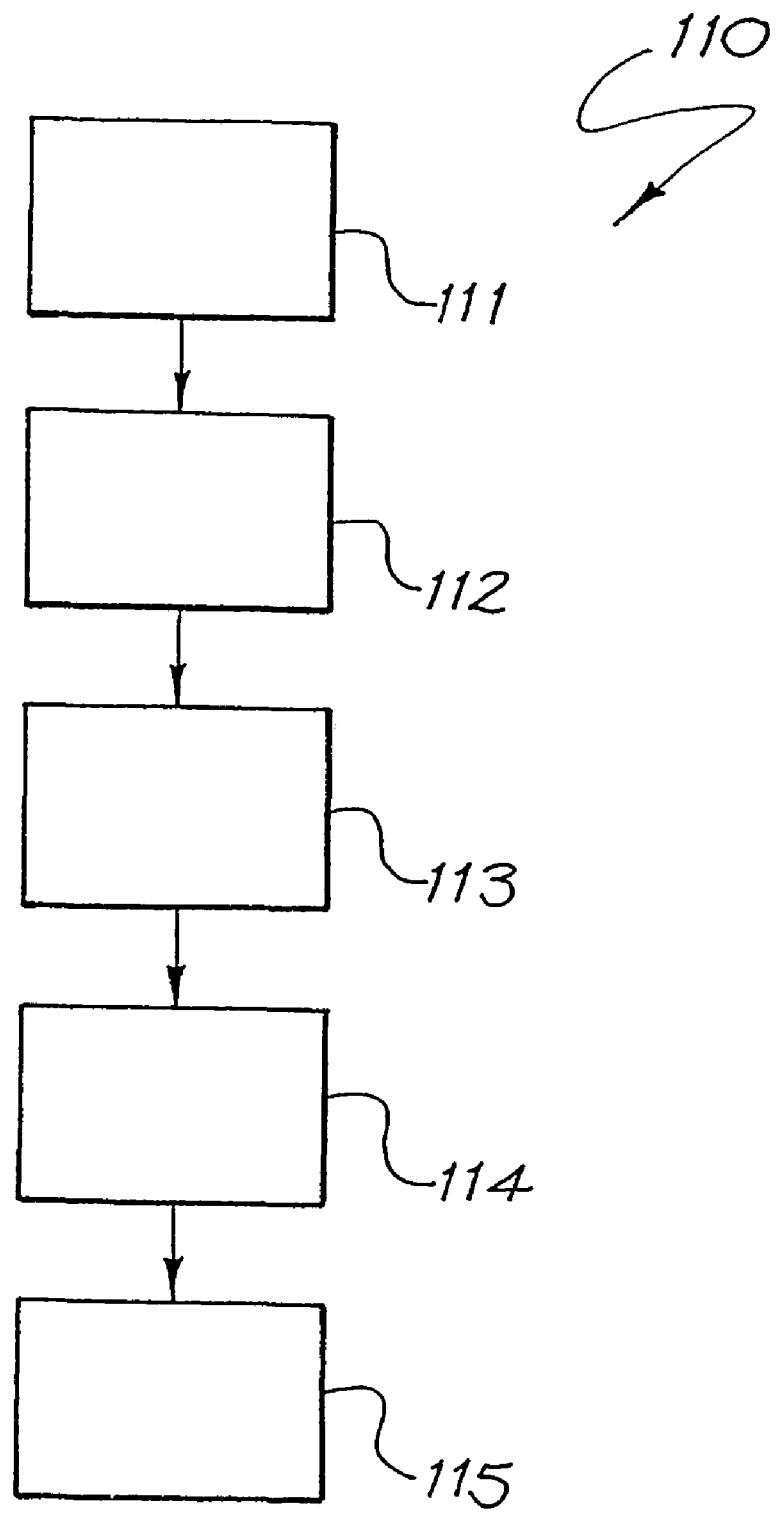
FIG. 24 is a flow chart depicting at least some of the steps of the method of forming an electrode array according to the present invention.

FIG. 24 is a flow chart of an example of some of the steps of a method according to a present invention, depicted generally as 110, for forming an electrode array that is suitable for use as a tissue-stimulating device within the human cochlea. The method 110 is more susceptible to automation that hitherto known techniques for manufacturing cochlea implant electrode arrays.

As depicted, the method 110 firstly comprises a step 111. Step 111 comprises coating a first surface of a sheet of platinum with a first layer of copper or other sacrificial type material. In the depicted method, platinum is used as it is a biocompatible material and is a proven material for use in cochlear implants manufactured using traditional techniques. The sheet is in the form of a foil and has a thickness between about 10 and 50 microns. Each sheet can have a dimension of about 50 mm×250 mm.

In step 111, the copper layer is plated to the first surface or underside of the sheet in a plating bath. Prior to the first layer being applied to the sheet, the sheet is though normally supported in a holder. Double-sided tape or other types of adhesives can be used to support the sheet to the holding member. The copper layer in this example of the method can have a thickness of about 100 microns. In another embodiment, the first layer can comprise a layer of electrically conductive film applied to the first surface of the sheet.

Once the first layer has been applied to the sheet, it is preferably polished. The purpose of the polishing is to ensure that the copper layer is as flat as possible.

The method 110 further comprises a step 112 in which an electrode array pattern is formed in the sheet of platinum. In this example, step 112 comprises removing portions of the platinum sheet therefrom such that at least the desired pattern of the electrode array and the wires remains.

In the example, step 112 comprises a process of using electrical discharge machining (EDM) to remove unwanted portions of the sheet. EDM relies on use of an electrode that generates a series of electrical discharges between the electrode and the sheet in a dielectric fluid. The electrical discharges serve to vaporise the sheet in the region adjacent the cutting tool.

Figure 17A:
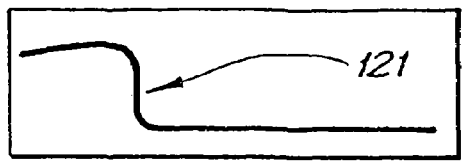
FIG. 17a is a plan view of an electrode tip for use in EDM equipment for use in one embodiment of the method according to the present invention.
Figure 18A:
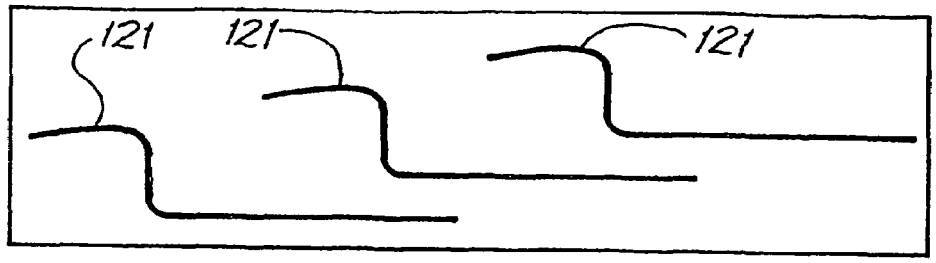
FIG. 18a is a plan view of another electrode tip for use in EDM equipment for use in one embodiment of the method according to the present invention.
Figure 18B:
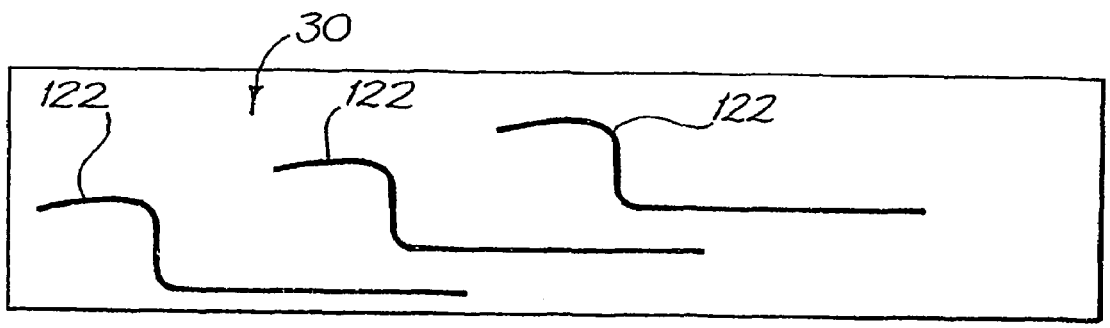
Figure 18C:
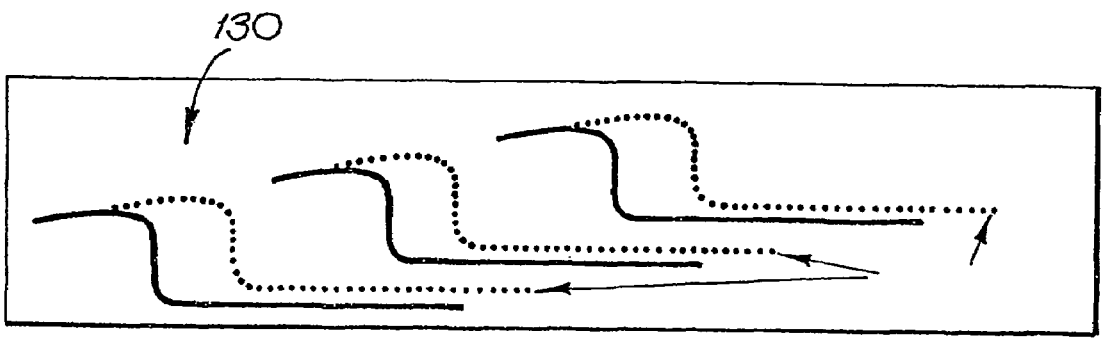
Figure 18D:
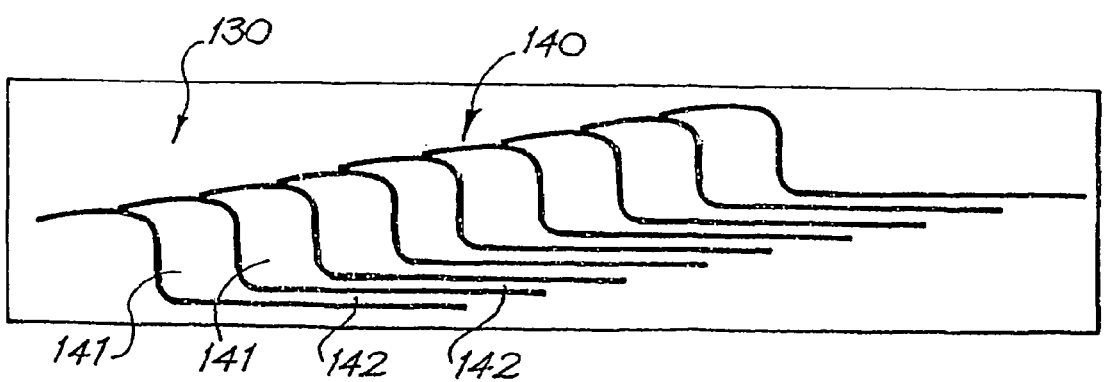
Figure 20:
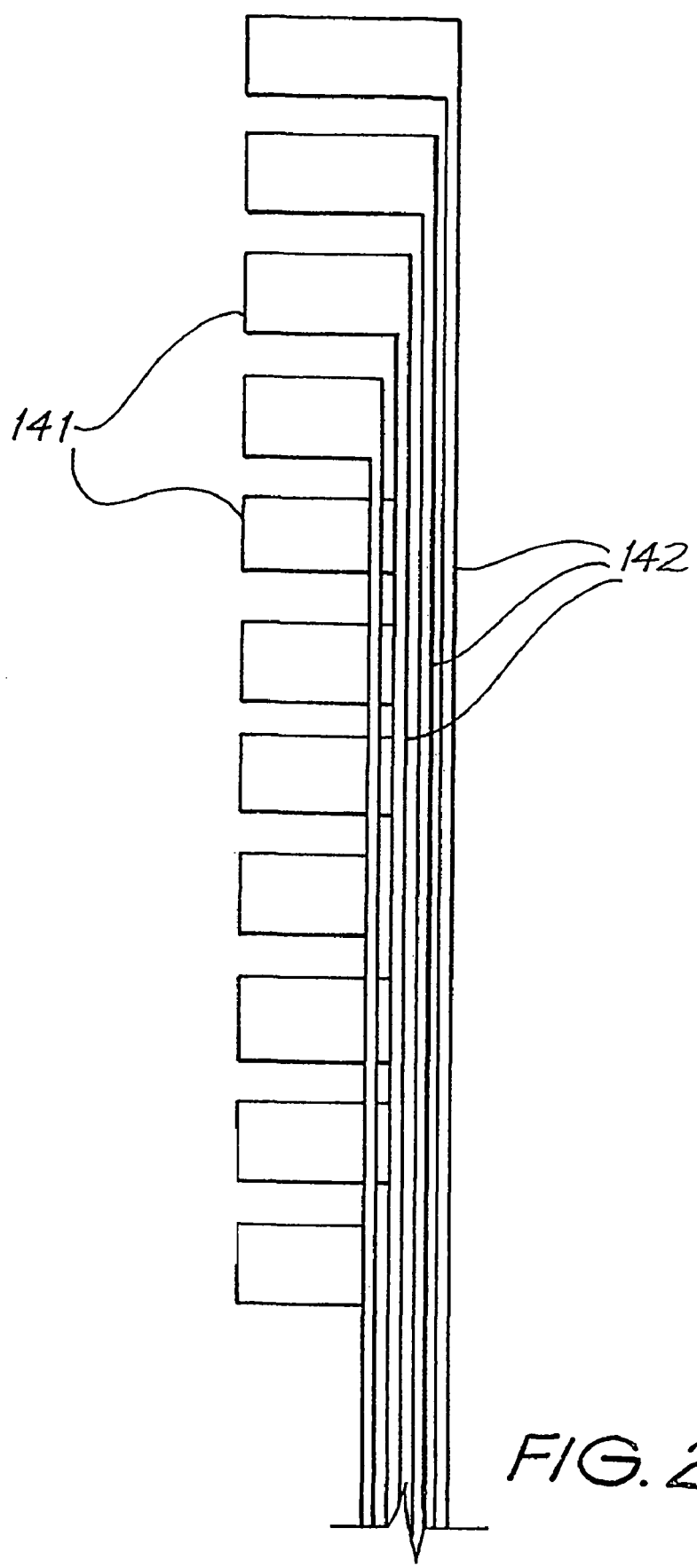
FIG. 20 is a drawing depicting how sets of electrodes formed using an embodiment of the method defined herein can be stacked on top of each other to form an electrode array suitable for use in a cochlear implant system.

As depicted in FIGS. 17a and 18a, the size and shape of the tip 121 of the electrode used in the EDM equipment together with the way in which the electrode is moved around the surface of the platinum and bought to bear on the surface, determines the size and shape of the portion 122 of the sheet 130 to be removed from the sheet 130 during step 112.

Figure 17B:
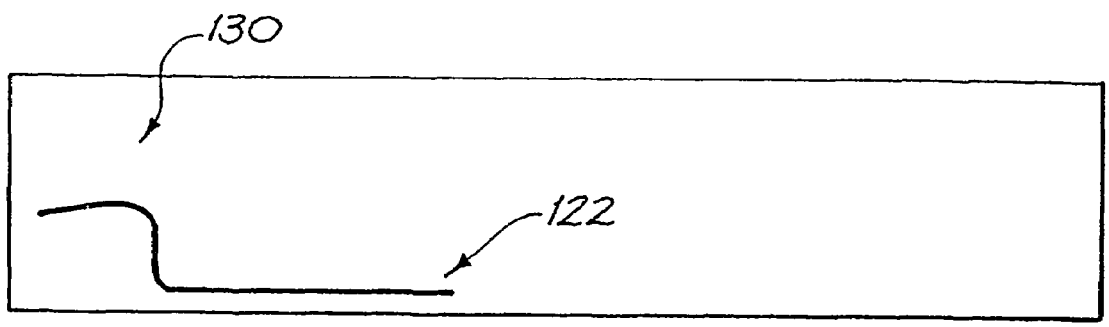
Figure 17C:
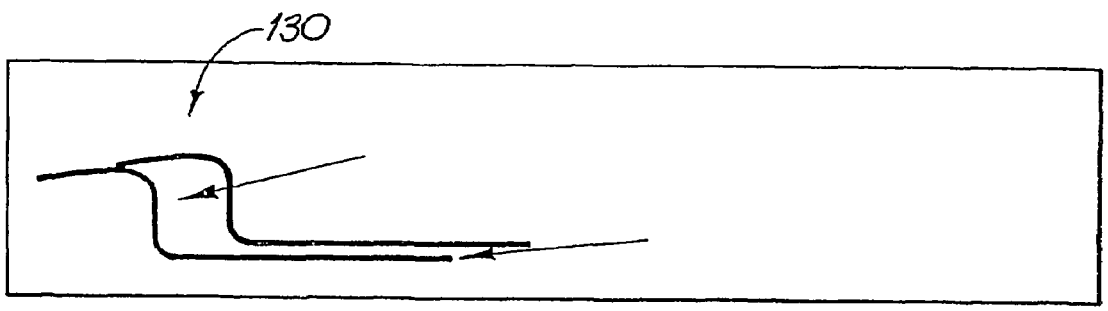
Figure 17D:
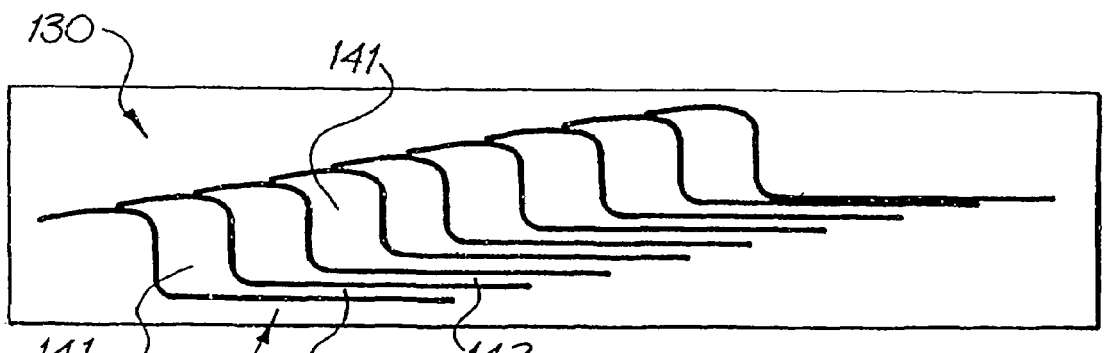

In the example depicted in FIG. 17a, the EDM equipment relies on use of a single tip 121 that is brought adjacent the sheet 130 at a number of different locations so as to remove differing portions 122 of the sheet 130. This multiple use of the tool serves to gradually build up the desired pattern of the electrode array 140. As can be seen in FIG. 17d, multiple use of the electrode 121 at different locations on the sheet 130 gradually leads to the creation of a linear array of discrete substantially rectangular electrodes 141 in the sheet 130, each electrode 141 having a conducting portion or wire 142 extending away therefrom to a location distal the electrode 141. Each conducting portion or wire can extend lineally away from its electrode.

As is depicted in FIG. 17d, the linear wires 142 are aligned in a parallel arrangement.

FIG. 18a depicts an alternative electrode tip arrangement to that depicted in FIG. 17a. In this arrangement, the EDM uses three tips 121 that simultaneously operate to remove three regions 122 of sheet 130 as depicted in FIG. 17b. As depicted in FIGS. 17c and 17d, through multiple uses of the EDM, an array of electrodes 141 and associated wires 142 are formed in the sheet 130. The advantage of the use of the arrangement depicted in FIG. 18a is that fewer uses of the EDM tip results in the formation of the same array 140.

Each electrode 141 formed in the sheet 130 has a size of about 0.4 mm²–0.5 mm².

During step 112, the EDM equipment is used in a manner such that it removes those portions of the platinum sheet 130 where desired and at least a portion of the copper layer that is plated to the sheet 130 therebeneath. The EDM equipment is operated in step 112 so as to not punch through the copper layer.

While not depicted, it will be appreciated that in step 112, those portions of the sheet 130 to be removed can be removed by other techniques, such as laser ablation, microknifing or milling to remove unwanted portions of the sheet.

The method 110 further comprises a step 113 of coating a second surface or topside of the platinum sheet with a layer of resiliently flexible and relatively electrically insulating material. This coating is made on the surface of the sheet 130 opposite to that which has received the copper layer.

In the example, step 113 comprises coating the second surface with a layer of parylene and/or silicone. Prior to this, at least the second surface of the sheet is cleaned and degreased. This coating is sprayed on to the second surface of the sheet. Other coating techniques could, however, be used including spinning, dipping, and adhering.

The resiliently flexible layer serves to hold the sheet in the pattern formed during step 112 during subsequent processing steps. By being relatively electrically insulating, the layer also acts as an insulating layer in the electrode array once formed, as is described in more detail below.

Prior to the coating of the second surface with the layer of resiliently flexible material, the method 110 can comprise an additional step in which the areas of sheet removed in step 112 are filled with a relatively electrically insulating material. The filler can be selected from the group comprising PVA, PEG, or a similar compound. The filler serves to prevent the layer of resiliently flexible material flowing into the gaps in the sheet formed by the removal of those portions of the sheet in step 112.

The method 110 comprises a still further step 114 in which the first layer of copper is removed from the first surface of the platinum sheet. In the depicted example, the copper layer is removed by dissolution in a bath. Other techniques can, however, be envisaged.

With the copper layer removed, the method 110 can still further comprise a step 115 in which a coating is applied to the first exposed surface or underside of the sheet 130. This coating preferably comprises a layer of resiliently flexible material. In the depicted example, the layer of material coated to the sheet 130 in step 115 is the same material coated to the second surface in step 113.

During step 115, the electrodes 141 are masked to ensure they remain uncovered with the layer of resiliently flexible material. The wires 142 are not masked and so are coated by this later of resiliently flexible material. In another arrangement, the layer coated to the sheet in step 115 can be removed where necessary, such as by laser ablation, so as to expose the covered electrodes 141.

Following step 115, the sheet 130 is preferably trimmed to remove the remaining portions of the sheet 130 that are not comprising the desired electrode array 140 and wires 142 extending therefrom. In the depicted example, the sheet 130 is trimmed with a knife. In another embodiment, a punch and die can be used to cut the electrode array and wires from the remaining portions of the original sheet 130.

While the electrode tip of the EDM equipment is depicted as having a particular arrangement depicted in FIGS. 17a and 18a, it will be appreciated that the electrode tip can have other arrangements. The result of one such other arrangement is depicted in FIG. 19. In this arrangement, use of the EDM tool results in the formation of five different electrodes sets, depicted as 151–155, respectively, on the one platinum sheet 130.

Each of the electrode sets, and corresponding wires, are formed in a manner such that their position with respect to each other is predetermined and kept constant throughout the process and in the final product.

In FIG. 19, the width of the wires of the electrode sets can be a between about 1 and 100 microns, more preferably 1 and 70 microns, and as such traditional manufacturing methods have problems producing such small dimensions. Further to this, the spacing between neighbouring wires can be between about 10 and 100 microns. Still further, the wires can be disposed for at least a portion of their lengths in a parallel arrangement.

Once each of the sets 151–155 are formed, each set can be trimmed from the sheet 130 and stacked one above the other to form an aligned array of electrodes 141. In the embodiment depicted in FIG. 19, the electrode array comprises 30 electrodes, with the array comprising 3 stacked sets of 7 electrodes, 1 set of five electrodes above these, and 1 set of 4 electrodes on top. Other combinations of sets can be, however, be envisaged.

While the sets of electrodes are stacked one upon the other, it will be appreciated that the actual position of the electrodes in each set are not necessarily vertically aligned. Rather, the set immediately above its lower set may be laterally offset so as to ensure the electrodes are visible from beneath the stack. A photo depicting a part of a longitudinal array of electrodes 141 formed using the method 110 is depicted as FIG. 20.

As depicted in FIG. 19, the wires 142 extending from each electrode 141 are of the same length. It can, however, be envisaged that the wires 142 could be formed with different lengths to account for the ultimate offset present when forming the stack.

Once the stack is formed, the hitherto at least substantially planar electrodes are preferably deformed so as to at least partially extend in a third dimension. In a preferred embodiment, each of the electrodes are curved out of the plane of the wires 142 for each set of electrodes. The curvature can be substantially semi-circular. A mandrel can be used to form the curvature in the electrodes.

Once the electrodes 141 have been deformed to have a substantially semi-circular curvature, each of the electrodes 141 are further folded about a longitudinal axis of the array 140. This folding of the electrodes 141 serves to bend the electrodes around the wires 142 of the array. The electrodes are preferably folded together and define a lumen that extends through the array 140. An example of the curvature of individual electrodes is depicted in FIG. 21.

Once the electrode array 140 is complete it is encapsulated in a further layer of a biocompatible silicone material to form a electrode carrier member 160. Silastic MDX 4-4210 is an example of one suitable silicone for use in the formation of the carrier member 160.

Figure 22:
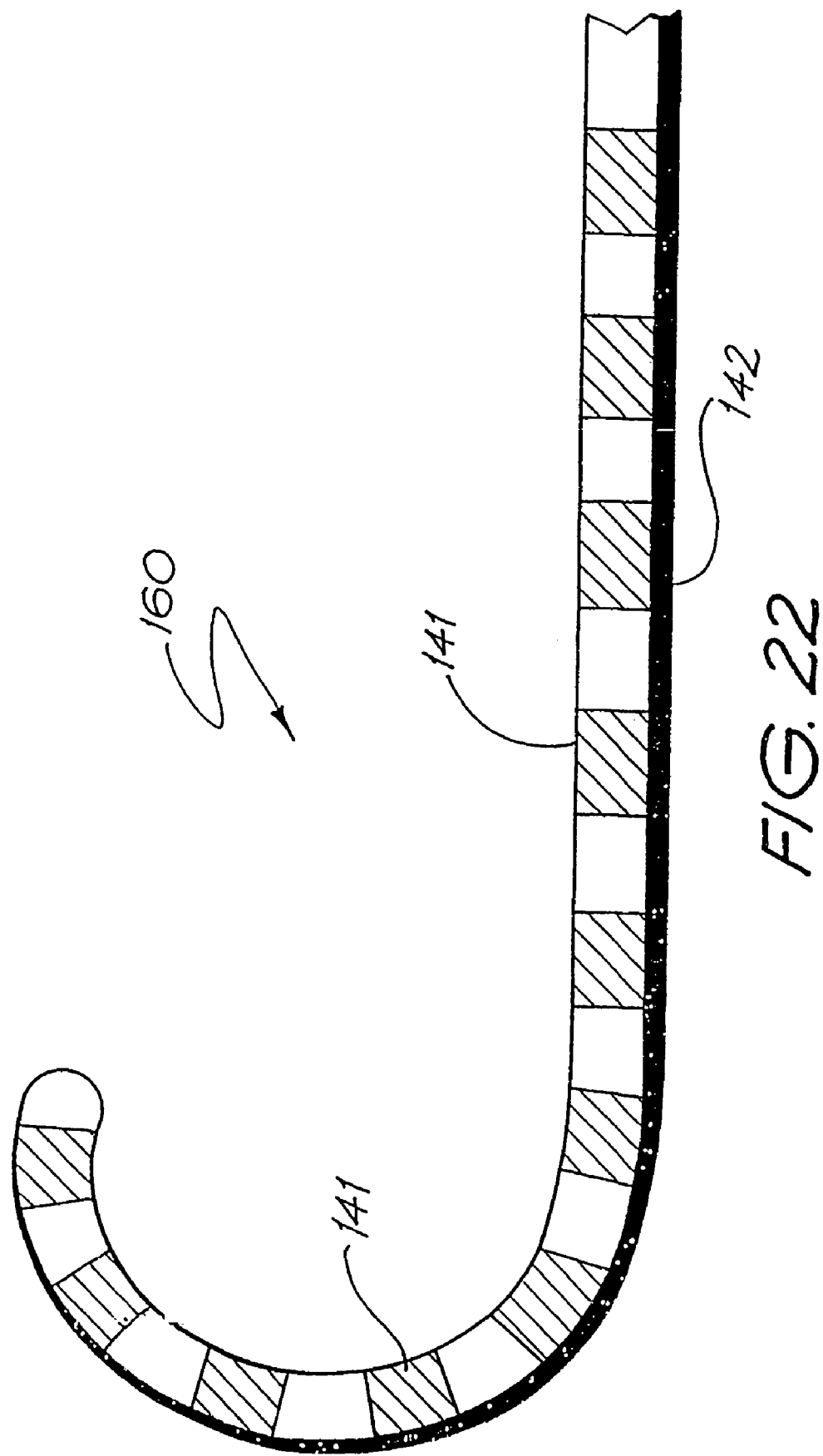
FIG. 22 is a drawing depicting the carrier member of FIG. 21 with the stylet retracted thereby allowing the carrier member to adopt a more pronounced curvature.
Figure 23:
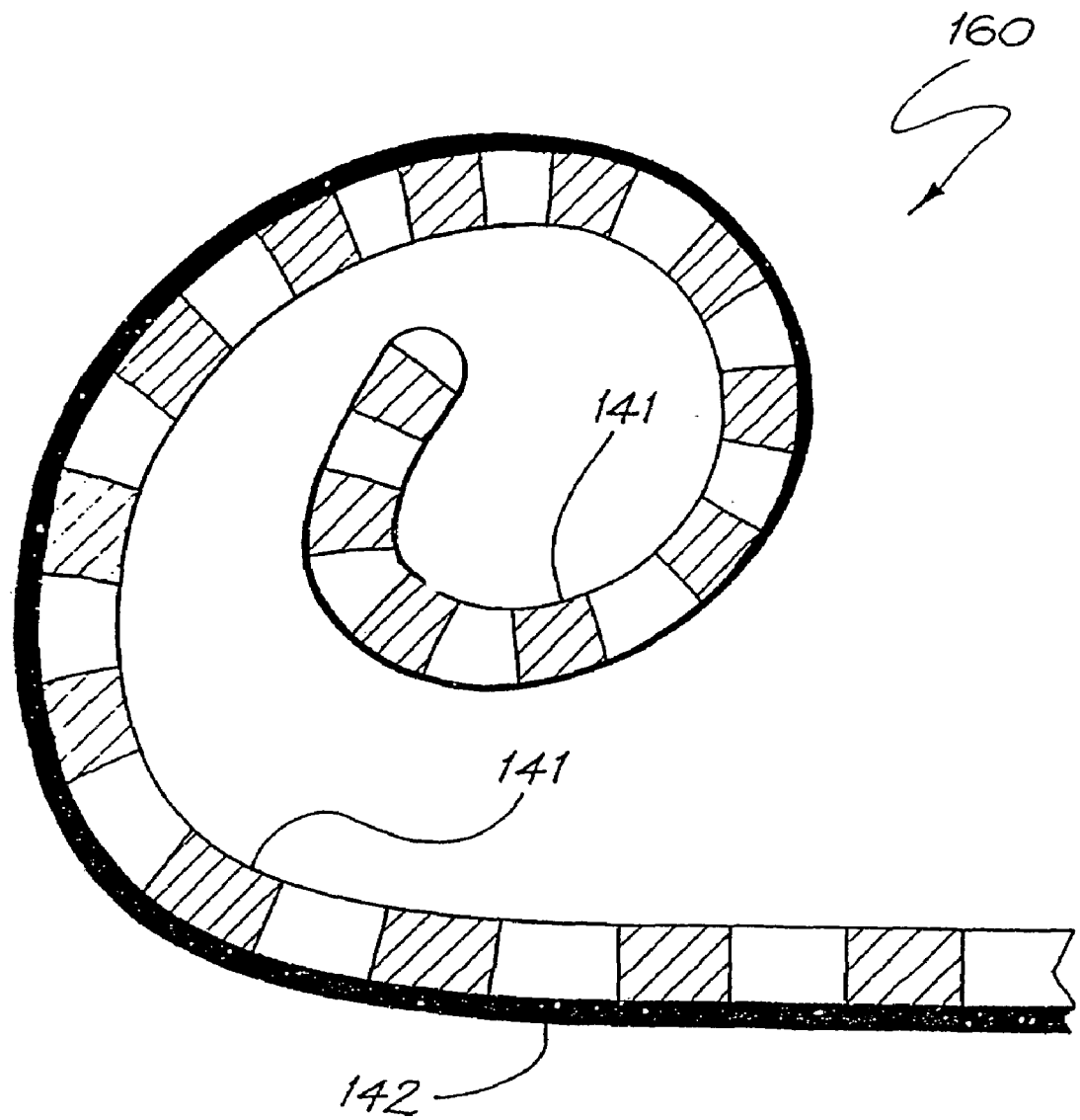
FIG. 23 is a drawing depicting the carrier member of FIG. 21 with the stylet fully retracted thereby allowing the carrier member to adopt its fully curved configuration.

The step of forming the carrier member 160 can comprise mounting the array 140 in a mould and filling the mould with the silicone and allowing it to cure. In this arrangement, the electrodes are positioned in the mould so as to not be coated with the silicone. In the arrangement depicted in FIGS. 21–23, the carrier member is moulded in a spirally-curved configuration and preferentially adopts this configuration unless straightened by the presence of a stylet 161 or other straightening means. In FIGS. 22 and 23, the degree of curvature of the depicted carrier member is to be taken as illustrative only. The electrode array and carrier member may be formed and moulded, respectively, to adopt a greater or lesser degree of curvature than that depicted when the stylet 161 is fully retracted.

Figure 21:
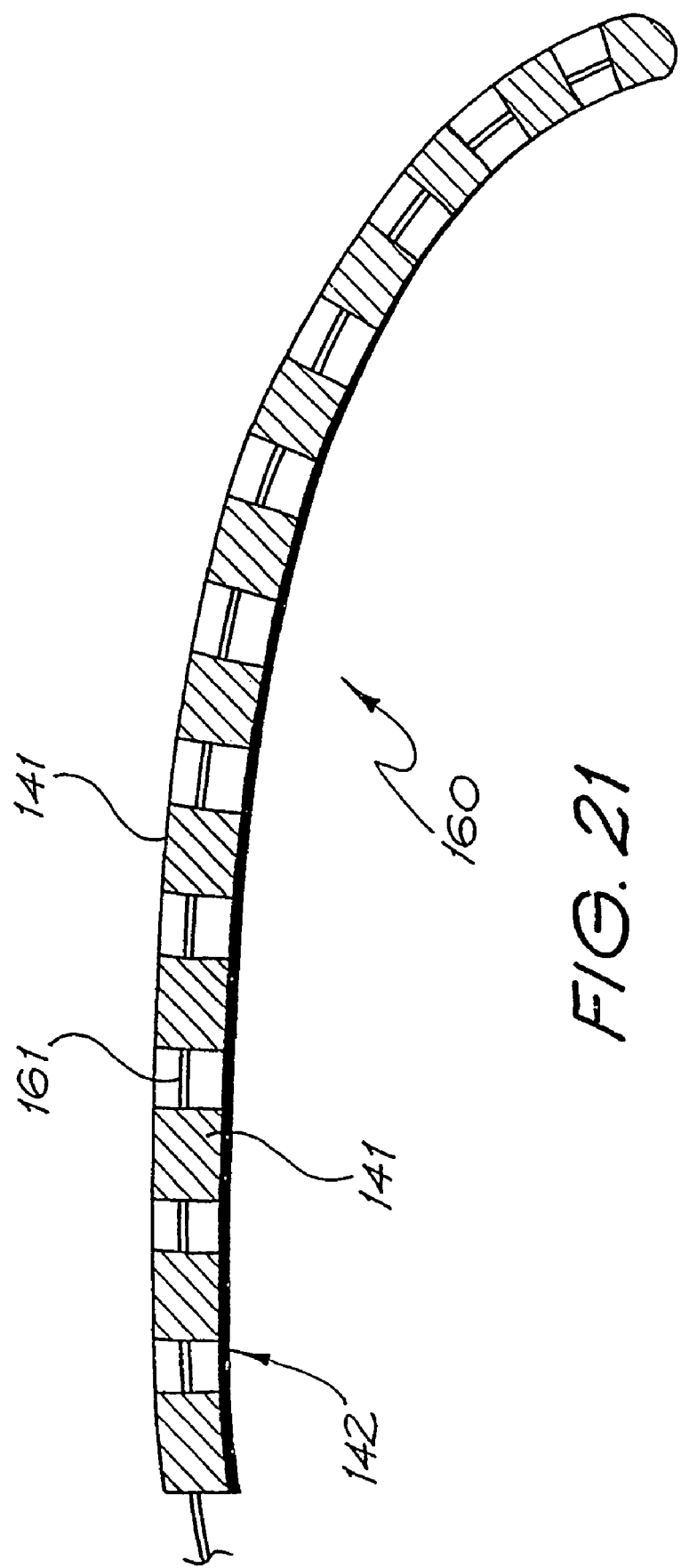
FIG. 21 is a drawing depicting a carrier member having an array of curved electrodes with a stylet positioned therein, the carrier being depicted in a configuration ready for insertion into the cochlea of an implantee.

In FIG. 21, it can be seen that the stylet 161 passes through a lumen in the carrier member 160 formed by the folding of the electrodes 141 as defined above.

While the depicted method relies on use of a layer of copper coated to the platinum sheet, the present application is also directed to an arrangement in which the platinum sheet is coated with a first layer of another material that is relatively electrically insulating. In this case, EDM cannot be used as described above. Rather, the unwanted portions of the platinum sheet 130 are preferably removed by another sheet portion removal technique, such as laser cutting, micro-knifing, chemical etching, stamping, or roller cutting. In this method, the first layer can comprise a polymeric material, such as a polycarbonate, polytetrafluoroethylene, polyimide, PAA, or PVA.

Use of the method 110 and the steps detailed herein results in the formation of a carrier member 160 for a cochlear implant system in which there has been no requirement to manually weld a wire to each electrode of the array. This serves to streamline the manufacturing process and allow greater automation thereof, resulting in suitable quality carrier members at a potentially lower cost.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of forming a device comprised of a predetermined pattern of discrete relatively electrically conductive regions and relatively electrically resistive regions, the method comprising a step of:
  working a sheet of electrically conductive material to remove predetermined portions therefrom to form said one or more discrete relatively conducting regions, wherein said sheet of electrically conductive material has a thickness no greater than about 100 microns,
  wherein the step of working the sheet includes a step of pressing the sheet of electrically conductive material using a pressing means to form a predetermined pattern of raised portions therein,
  wherein the working step comprises using an embossing tool,
  wherein the sheet of electrically conductive material is a planar sheet that is mountable relative to the embossing tool in the pressing means,
  wherein during the working step the sheet is placed above and on the embossing tool and a layer of backing material is then placed on top of the sheet before operation of the pressing means, wherein the embossing tool with the embossed sheet and layer of backing material positioned thereon, are relatively removable from within the pressing means.

2. A method of forming a device comprised of a predetermined pattern of discrete relatively electrically conductive regions and relatively electrically resistive regions, the method comprising a step of:
working a sheet of electrically conductive material to remove predetermined portions therefrom to form said one or more discrete relatively conducting regions, wherein said sheet of electrically conductive material has a thickness no greater than about 100 microns,
wherein the step of working the sheet includes a step of pressing the sheet of electrically conductive material using a pressing means to form a predetermined pattern of raised portions therein,
wherein the working step comprises using an embossing tool,
wherein the sheet of electrically conductive material is a planar sheet that is mountable relative to the embossing tool in the pressing means,
wherein during the working step the sheet is placed above and on the embossing tool and a layer of backing material is then placed on top of the sheet before operation of the pressing means,
wherein following pressing of the sheet of electrically conducting material, the layer of backing material is removable from the embossed sheet.

3. A method of forming a device comprised of a predetermined pattern of discrete relatively electrically conductive regions and relatively electrically resistive regions, the method comprising a step of:
working a sheet of electrically conductive material to remove predetermined portions therefrom to form said one or more discrete relatively conducting regions, wherein said sheet of electrically conductive material has a thickness no greater than about 100 microns,
wherein the step of working the sheet includes a step of pressing the sheet of electrically conductive material to form an embossed sheet having a predetermined pattern of raised portions therein,
wherein the working step comprises using an embossing tool,
wherein an abrading means is used in an abrading step to remove unwanted portions from the embossed sheet,
wherein prior to the abrading step the embossed sheet is adhered by a layer of an adhesive to a support base.

4. The method of forming a device of claim 3 wherein the embossed sheet is placed on the adhesive layer such that the raised pattern extends outwardly away from the adhesive.

5. The method of forming a device of claim 4 wherein after the abrading step the method further includes a step of encapsulating at least one surface of the embossed sheet in an electrically insulating encapsulant.

6. The method of forming a device of claim 5 wherein after the step of encapsulating said at least one surface, the device is removed from the support base so providing a plurality of separate electrically independent conductive portions having a layer of encapsulant encapsulated on one side thereof.

7. A method of forming a device comprised of a predetermined pattern of relatively electrically conductive regions and relatively electrically resistive regions, the method comprising the steps of:
(i) coating at least a first surface of a sheet of electrically conductive material with a first layer of another electrically conductive material;

(ii) forming a predetermined pattern in the sheet of electrically conductive material by removing portions of the sheet therefrom such that at least the pattern of electrically conductive regions remain;
(iii) coating a second surface of the sheet of electrically conductive material with a layer of resiliently flexible material; and
(iv) removing the first layer from the first surface of said sheet.

8. The method of forming a device of claim 7 wherein the device is an electrode array and step (ii) comprises forming a predetermined electrode array pattern in the sheet.

9. The method of forming a device of claim 7 wherein the sheet of electrically conductive material is a biocompatible metallic material.

10. The method of forming a device of claim 9 wherein the sheet is a platinum foil having a thickness no greater than about 50 microns.

11. The method of forming a device of claim 10 wherein the thickness of the platinum foil is no greater than about 20 microns.

12. The method of forming a device of claim 7 wherein the first layer of electrically conductive material comprises a metal.

13. The method of forming a device of claim 12 wherein the first layer of metal is a layer of copper.

14. The method of forming a device of claim 7 wherein step (ii) comprises using electrical discharge machining (EDM) to remove unwanted portions of the sheet, the EDM equipment having a cutting tool comprising an electrode.

15. The method of forming a device of claim 14 wherein the cutting tool has a size and shape that at least substantially matches the size and shape of the portion of the sheet to be removed from the sheet during the electrical discharge machining step comprising step (ii).

16. The method of forming a device of claim 15 wherein the tool is brought adjacent the sheet at a number of different locations so as to remove differing portions of the sheet, the multiple use of the tool serving to gradually build up the predetermined pattern.

17. The method of forming a device of claim 16 wherein the cutting tool is used to form at least one linear array of discrete stimulating pads or electrodes in the sheet, each pad preferably having a conducting portion extending away therefrom to a location distal the pad.

18. The method of forming a device of claim 17 wherein each conducting portion extends linearly away from its pad, the linear conducting portions being aligned in a parallel arrangement.

19. The method of forming a device of claim 18 wherein each pad has an areal dimension of less than 0.5 mm$^2$.

20. The method of forming a device of claim 18 wherein each conducting portion has a width of between about 1 and 100 microns, more preferably between 1 and 70 microns.

21. The method of forming a device of claim 18 wherein each conductive portion is electrically insulated from its neighbouring conductive wire, the spacing between neighbouring wires being between about 10 and 100 microns.

22. The method of forming a device of claim 14 wherein the cutting tool removes the platinum where desired and at least a portion of the first layer therebeneath.

23. The method of forming a device of claim 7 wherein step (iii) comprises coating the second surface with a layer of parylene and/or silicone.

24. The method of forming a device of claim 23 wherein prior to the coating of the second surface with the layer of resiliently flexible material, the method comprises an additional step in which the areas of sheet removed in step (ii) are filled with a relatively electrically insulating material.

25. The method of forming a device of claim 7 wherein the method further comprises the following step:
  (v) coating the exposed first surface of the sheet with a layer of resiliently flexible material.

26. The method of forming a device of claim 25 wherein the layer of material coated to the sheet in step (v) comprises the same material coated to the second surface in step (iii).

27. The method of forming a device of claim 26 wherein during step (v), the electrically conductive regions formed in step (ii) are masked to ensure they remain uncovered with the layer of resiliently flexible material and the conducting portions are not masked and so coated by this layer of resiliently flexible material.

28. The method of forming a device of claim 26 wherein following step (v), the sheet is trimmed to remove the remaining portions of the sheet that do not comprise the pattern of electrically conductive regions.

29. The method of forming a device 28 wherein all of the required number of electrically conductive regions for a device are formed in different regions of a single platinum sheet.

30. The method of forming a device of claim 29 wherein each sheet has a plurality of respective sets of electrically conductive regions formed therein, the sets being adapted to form a single electrode array.

31. The method of forming a device of claim 30 wherein once each of the sets are formed on the sheet, each trimmed set is stacked one above the other to form an aligned array of stimulating pads.

32. The method of forming a device of claim 31 wherein the electrode array comprises 30 stimulating pads, with the electrode array comprising 5 different sets of pads that have been formed in a single sheet, trimmed, and then stacked to form a single electrode array.

33. The method of forming a device of claim 32 wherein the electrode array comprises 3 sets of 7 pads, 1 set of five pads and 1 set of 4 pads, the 3 sets of 7 pads being stacked one on top of the other, the set of five pads being stacked on these sets, and with the set of 4 pads on top of the stack.

34. The method of forming a device of claim 33 wherein once the stack is formed, the hitherto at least substantially planar pads are curved out of the plane of the conducting portions for each set of pads.

35. The method of forming a device of claim 34 wherein once the stimulating pads have been deformed to have a curvature, each of the stimulating pads are further folded about a longitudinal axis of the array.

36. The method of forming a device of claim 34 wherein once the electrode array is complete it is encapsulated in a further layer of a biocompatible material to form an electrode carrier member.

37. The method of forming a device comprised of a predetermined pattern of relatively electrically conductive regions and relatively electrically resistive regions, the method comprising the steps of:
  (i) mounting a sheet of electrically conductive material in an electrical discharge machining (EDM) device, the device having a discharge electrode of a predetermined shape;
  (ii) programming the EDM device to bring the electrode adjacent the sheet; and
  (iii) operating the EDM device to remove a portion of the sheet corresponding to the shape of the electrode.

38. The method of forming a device of claim 37 wherein the sheet prior to mounting in the EDM device is firstly coated on at least a first surface thereof with a layer of electrically conductive material.

39. The method of forming a device of claim 38 wherein the layer of electrically conductive material comprises a layer of metal, such as copper.

40. The method of forming a device of claim 38 wherein once the pattern has been formed in the sheet, a second surface of the sheet of electrically conductive material can be coated with a layer of resiliently flexible material.

41. The method of forming a device of claim 40 wherein once the second surface of the sheet has been coated with the layer of resiliently flexible material, the layer of electrically conductive material can be removed from the first surface of said sheet.

42. The method of forming a device of claim 37 wherein the device is an electrode array.

43. The method of forming a device of claim 37 wherein the sheet of electrically conductive material is a platinum sheet having a thickness no greater than 50 microns.

\* \* \* \* \*

UNITED STATES PATENT AND TRADEMARK OFFICE
CERTIFICATE OF CORRECTION

PATENT NO. : 7,240,416 B2  Page 1 of 1
APPLICATION NO. : 10/477434
DATED : July 10, 2007
INVENTOR(S) : Dusan Milojevic et al.

It is certified that error appears in the above-identified patent and that said Letters Patent is hereby corrected as shown below:

In the Claims

| | |
|---|---|
| Column 28, line 67, Claim 1 | After "means,", Insert --and-- |
| Column 29, line 25, Claim 2 | After "means,", Insert --and-- |
| Column 31, line 20, Claim 29 | After "a device", Insert --of claim-- |

Signed and Sealed this

Thirteenth Day of May, 2008

JON W. DUDAS
*Director of the United States Patent and Trademark Office*